US012765875B2

(12) United States Patent
Wellman

(10) Patent No.: US 12,765,875 B2
(45) **Date of Patent: *Oct. 20, 2026**

(54) STAPLE CARTRIDGE FOR A SURGICAL INSTRUMENT

(71) Applicant: INTUITIVE SURGICAL OPERATIONS, INC., Sunnyvale, CA (US)

(72) Inventor: Ashley Wellman, Palo Alto, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/229,215

(22) Filed: Jun. 5, 2025

(65) Prior Publication Data

US 2025/0295410 A1 Sep. 25, 2025

Related U.S. Application Data

(63) Continuation of application No. 18/406,333, filed on Jan. 8, 2024, now Pat. No. 12,349,905, which is a (Continued)

(51) Int. Cl.
*A61B 17/072* (2006.01)
*A61B 17/064* (2006.01)
*A61B 34/30* (2016.01)

(52) U.S. Cl.
CPC ...... *A61B 17/07207* (2013.01); *A61B 17/064* (2013.01); *A61B 2017/07257* (2013.01); (Continued)

(58) Field of Classification Search
CPC ............ A61B 17/064; A61B 17/07207; A61B 2017/07257; A61B 2017/07271; (Continued)

(56) References Cited

U.S. PATENT DOCUMENTS

| | | | |
|---|---|---|---|
| 75,364 | A | 3/1868 | Case |
| 3,792,597 | A | 2/1974 | Orain et al. |

(Continued)

FOREIGN PATENT DOCUMENTS

| | | | |
|---|---|---|---|
| AU | 2014259544 | A1 | 9/2015 |
| CN | 103889344 | A | 6/2014 |

(Continued)

OTHER PUBLICATIONS

Anonymous: "Slip Joint Pliers—Wikipedia," Sep. 2017, 1 Pages. Retrieved from internet URL:https:/en.wikipedia.org/w/index.php?tilte=split_joint_pliers&oldid=801407143.

(Continued)

*Primary Examiner* — Linda J. Hodge
(74) *Attorney, Agent, or Firm* — Farber LLC

(57) ABSTRACT

The present disclosure provides a staple cartridge for a surgical instrument having a staple and a staple pusher. The staple pusher has a recess forming a pocket in its top surface for receiving at least the backspan of the staple. The pocket is at least partially surrounded by a circumferential supporting element in the staple pusher body to support the backspan. The pocket provides additional vertical space and support for the staple such that a smaller staple cartridge may provide a substantially similar performance as conventional staple cartridges, allowing for a more compact and maneuverable surgical instrument. In addition, the pocket in the staple pusher allows for a staple having a larger bend radius than conventional staples, thereby providing additional support for the staple and minimizing malformation of the staple during use.

19 Claims, 13 Drawing Sheets

Related U.S. Application Data continuation of application No. 17/605,230, filed as application No. PCT/US2020/033481 on May 18, 2020, now Pat. No. 11,896,224.

(60) Provisional application No. 62/855,371, filed on May 31, 2019.

(52) U.S. Cl.
CPC ............... *A61B 2017/07271* (2013.01); *A61B 2017/07278* (2013.01); *A61B 2034/302* (2016.02)

(58) Field of Classification Search
CPC ........... A61B 2017/07278; A61B 2017/07235; A61B 2017/07242; A61B 2017/07228; A61B 2017/00314; A61B 2034/30; A61B 34/35
See application file for complete search history.

(56) References Cited

U.S. PATENT DOCUMENTS

| | | | |
|---|---|---|---|
| D231,902 | S | 6/1974 | Olson |
| D236,083 | S | 7/1975 | Olson |
| D236,427 | S | 8/1975 | Olson |
| 4,305,539 | A | 12/1981 | Korolkov et al. |
| 4,319,576 | A | 3/1982 | Rothfuss |
| 4,352,276 | A | 10/1982 | Smith |
| 4,403,892 | A | 9/1983 | Kane |
| 4,407,286 | A | 10/1983 | Noiles et al. |
| 4,429,695 | A | 2/1984 | Green |
| 4,509,518 | A | 4/1985 | McGarry et al. |
| 4,509,932 | A | 4/1985 | Weible |
| 4,605,001 | A | 8/1986 | Rothfuss et al. |
| 4,608,981 | A | 9/1986 | Rothfuss et al. |
| 4,610,383 | A | 9/1986 | Rothfuss et al. |
| 4,633,874 | A | 1/1987 | Chow et al. |
| 4,767,044 | A | 8/1988 | Green |
| 4,809,695 | A | 3/1989 | Gwathmey et al. |
| 4,848,637 | A | 7/1989 | Pruitt |
| 4,892,244 | A | 1/1990 | Fox et al. |
| 4,930,503 | A | 6/1990 | Pruitt |
| 4,978,049 | A | 12/1990 | Green |
| 5,007,300 | A | 4/1991 | Siva |
| 5,027,834 | A | 7/1991 | Pruitt |
| 5,040,715 | A | 8/1991 | Green et al. |
| 5,133,735 | A | 7/1992 | Slater et al. |
| 5,133,736 | A | 7/1992 | Bales, Jr. et al. |
| 5,142,931 | A | 9/1992 | Menahem |
| 5,147,357 | A | 9/1992 | Rose et al. |
| 5,180,092 | A | 1/1993 | Crainich |
| 5,242,457 | A | 9/1993 | Akopov et al. |
| 5,275,323 | A | 1/1994 | Schulze et al. |
| 5,307,976 | A | 5/1994 | Olson et al. |
| 5,312,023 | A | 5/1994 | Green et al. |
| 5,316,435 | A | 5/1994 | Mozingo |
| 5,334,183 | A | 8/1994 | Wuchinich |
| 5,342,395 | A | 8/1994 | Jarrett et al. |
| 5,342,396 | A | 8/1994 | Cook |
| 5,366,133 | A | 11/1994 | Geiste |
| 5,452,836 | A | 9/1995 | Huitema et al. |
| 5,452,837 | A | 9/1995 | Williamson, IV et al. |
| 5,465,895 | A | 11/1995 | Knodel et al. |
| 5,480,089 | A | 1/1996 | Blewett |
| 5,484,095 | A | 1/1996 | Green et al. |
| 5,484,451 | A | 1/1996 | Akopov et al. |
| 5,487,500 | A | 1/1996 | Knodel et al. |
| 5,497,931 | A | 3/1996 | Nakamura |
| 5,533,521 | A | 7/1996 | Granger |
| 5,540,375 | A | 7/1996 | Bolanos et al. |
| 5,554,164 | A | 9/1996 | Wilson et al. |
| 5,560,530 | A | 10/1996 | Bolanos et al. |
| 5,562,239 | A | 10/1996 | Boiarski et al. |
| 5,564,615 | A | 10/1996 | Bishop et al. |
| 5,571,116 | A | 11/1996 | Bolanos et al. |
| 5,571,285 | A | 11/1996 | Chow et al. |
| 5,573,534 | A | 11/1996 | Stone |
| 5,573,543 | A | 11/1996 | Akopov et al. |
| 5,607,449 | A | 3/1997 | Tontarra |
| 5,615,820 | A | 4/1997 | Viola |
| 5,624,452 | A | 4/1997 | Yates |
| 5,628,446 | A | 5/1997 | Geiste et al. |
| 5,632,432 | A | 5/1997 | Schulze et al. |
| 5,651,491 | A | 7/1997 | Heaton et al. |
| 5,652,849 | A | 7/1997 | Conway et al. |
| 5,667,626 | A | 9/1997 | Cayford et al. |
| 5,673,840 | A | 10/1997 | Schulze et al. |
| 5,673,842 | A | 10/1997 | Bittner et al. |
| 5,676,674 | A | 10/1997 | Bolanos et al. |
| 5,688,269 | A | 11/1997 | Newton et al. |
| 5,690,269 | A | 11/1997 | Bolanos et al. |
| 5,693,042 | A | 12/1997 | Boiarski et al. |
| 5,697,542 | A | 12/1997 | Knodel et al. |
| 5,700,270 | A | 12/1997 | Peyser et al. |
| 5,700,276 | A | 12/1997 | Benecke |
| 5,704,534 | A | 1/1998 | Huitema et al. |
| 5,709,680 | A | 1/1998 | Yates et al. |
| 5,738,474 | A | 4/1998 | Blewett |
| 5,752,644 | A | 5/1998 | Bolanos et al. |
| 5,752,973 | A | 5/1998 | Kieturakis et al. |
| 5,762,255 | A | 6/1998 | Chrisman et al. |
| 5,762,256 | A | 6/1998 | Mastri et al. |
| 5,779,130 | A | 7/1998 | Alesi et al. |
| 5,782,396 | A | 7/1998 | Mastri et al. |
| 5,792,135 | A | 8/1998 | Madhani et al. |
| 5,820,009 | A | 10/1998 | Melling et al. |
| 5,826,776 | A | 10/1998 | Schulze et al. |
| 5,833,695 | A | 11/1998 | Yoon |
| 5,865,361 | A | 2/1999 | Milliman et al. |
| 5,871,135 | A | 2/1999 | Williamson, IV et al. |
| 5,911,353 | A | 6/1999 | Bolanos et al. |
| 5,915,616 | A | 6/1999 | Viola et al. |
| 5,919,198 | A | 7/1999 | Graves, Jr. et al. |
| 5,941,442 | A | 8/1999 | Geiste et al. |
| 5,954,259 | A | 9/1999 | Viola et al. |
| 5,959,892 | A | 9/1999 | Lin et al. |
| 6,032,849 | A | 3/2000 | Mastri et al. |
| 6,050,996 | A | 4/2000 | Schmaltz et al. |
| 6,079,606 | A | 6/2000 | Milliman et al. |
| 6,113,598 | A | 9/2000 | Baker |
| 6,126,666 | A | 10/2000 | Trapp et al. |
| 6,174,309 | B1 | 1/2001 | Wrublewski et al. |
| 6,202,914 | B1 | 3/2001 | Geiste et al. |
| 6,241,139 | B1 | 6/2001 | Milliman et al. |
| 6,250,532 | B1 | 6/2001 | Green et al. |
| 6,312,426 | B1 | 11/2001 | Goldberg et al. |
| 6,330,956 | B1 | 12/2001 | Willinger |
| 6,330,965 | B1 | 12/2001 | Milliman et al. |
| 6,443,973 | B1 | 9/2002 | Whitman |
| 6,488,196 | B1 | 12/2002 | Fenton, Jr. |
| 6,503,259 | B2 | 1/2003 | Huxel et al. |
| 6,582,451 | B1 | 6/2003 | Marucci et al. |
| 6,585,735 | B1 | 7/2003 | Frazier et al. |
| 6,644,532 | B2 | 11/2003 | Green et al. |
| 6,656,193 | B2 | 12/2003 | Grant et al. |
| 6,669,073 | B2 | 12/2003 | Milliman et al. |
| 6,692,363 | B1 | 2/2004 | Heutschi et al. |
| 6,770,072 | B1 | 8/2004 | Truckai et al. |
| 6,783,524 | B2 | 8/2004 | Anderson et al. |
| 6,786,382 | B1 | 9/2004 | Hoffman |
| 6,793,652 | B1 | 9/2004 | Whitman et al. |
| 6,817,974 | B2 | 11/2004 | Cooper et al. |
| 6,840,938 | B1 | 1/2005 | Morley et al. |
| 6,877,647 | B2 | 4/2005 | Green et al. |
| 6,905,057 | B2 | 6/2005 | Swayze et al. |
| 6,953,139 | B2 | 10/2005 | Milliman et al. |
| 6,955,608 | B1 | 10/2005 | Lutz |
| 6,959,852 | B2 | 11/2005 | Shelton, IV et al. |
| 6,964,363 | B2 | 11/2005 | Wales et al. |
| 6,978,921 | B2 | 12/2005 | Shelton, IV et al. |
| 6,978,922 | B2 | 12/2005 | Bilotti et al. |
| 6,981,941 | B2 | 1/2006 | Whitman et al. |
| 6,985,133 | B1 | 1/2006 | Rodomista et al. |

(56) References Cited

U.S. PATENT DOCUMENTS 6,986,451 B1 1/2006 Mastri et al.
6,988,649 B2 1/2006 Shelton, IV et al.
7,000,818 B2 2/2006 Shelton, IV et al.
7,000,819 B2 2/2006 Swayze et al.
7,044,352 B2 5/2006 Shelton, IV et al.
7,044,353 B2 5/2006 Mastri et al.
7,055,730 B2 6/2006 Ehrenfels et al.
7,055,731 B2 6/2006 Shelton, IV et al.
7,059,508 B2 6/2006 Shelton, IV et al.
7,070,083 B2 7/2006 Jankowski
7,114,642 B2 10/2006 Whitman
7,128,253 B2 10/2006 Mastri et al.
7,140,527 B2 11/2006 Ehrenfels et al.
7,140,528 B2 11/2006 Shelton, IV et al.
7,258,262 B2 8/2007 Mastri et al.
7,296,722 B2 11/2007 Ivanko
7,308,998 B2 12/2007 Mastri et al.
7,328,828 B2 2/2008 Ortiz et al.
7,380,695 B2 6/2008 Doll et al.
7,380,696 B2 6/2008 Shelton, IV et al.
7,398,908 B2 7/2008 Holsten et al.
7,401,721 B2 7/2008 Holsten et al.
7,407,075 B2 8/2008 Holsten et al.
7,455,676 B2 11/2008 Holsten et al.
7,472,814 B2 1/2009 Mastri et al.
7,481,349 B2 1/2009 Holsten et al.
7,491,202 B2 2/2009 Odom et al.
7,494,039 B2 2/2009 Racenet et al.
7,561,141 B2 7/2009 Shahoian et al.
7,565,993 B2 7/2009 Milliman et al.
7,588,174 B2 9/2009 Holsten et al.
7,654,431 B2 2/2010 Hueil et al.
7,658,312 B2 2/2010 Vidal et al.
7,673,783 B2 3/2010 Morgan et al.
7,699,835 B2 4/2010 Lee et al.
7,721,930 B2 5/2010 McKenna et al.
7,726,539 B2 6/2010 Holsten et al.
7,770,774 B2 8/2010 Mastri et al.
7,780,577 B2 8/2010 Arnold
7,794,475 B2 9/2010 Hess et al.
7,832,611 B2 11/2010 Boyden et al.
7,837,079 B2 11/2010 Holsten et al.
7,866,526 B2 1/2011 Green et al.
7,942,303 B2 5/2011 Shah et al.
7,950,561 B2 5/2011 Aranyi
8,070,035 B2 12/2011 Holsten et al.
8,083,118 B2 12/2011 Milliman et al.
8,127,975 B2 3/2012 Olson et al.
8,157,152 B2 4/2012 Holsten et al.
8,272,553 B2 9/2012 Mastri et al.
8,308,042 B2 11/2012 Aranyi
8,348,127 B2 1/2013 Marczyk
8,365,972 B2 2/2013 Aranyi et al.
8,371,492 B2 2/2013 Aranyi et al.
8,439,246 B1 5/2013 Knodel
8,490,851 B2 7/2013 Blier et al.
8,551,091 B2 10/2013 Couture et al.
8,573,465 B2 11/2013 Shelton, IV
8,579,178 B2 11/2013 Holsten et al.
8,608,047 B2 12/2013 Holsten et al.
8,672,206 B2 3/2014 Aranyi et al.
8,672,939 B2 3/2014 Garrison
8,685,016 B2 4/2014 Wham et al.
8,701,960 B1 4/2014 Manoux et al.
8,783,541 B2 7/2014 Shelton, IV et al.
8,800,841 B2 8/2014 Ellerhorst et al.
8,834,518 B2 9/2014 Faller et al.
8,851,355 B2 10/2014 Aranyi et al.
8,852,174 B2 10/2014 Burbank
8,858,547 B2 10/2014 Brogna
8,864,010 B2 10/2014 Williams
8,876,857 B2 11/2014 Burbank
8,905,287 B2 12/2014 Racenet et al.
8,925,785 B2 1/2015 Holsten et al.
9,010,606 B2 4/2015 Aranyi et al.
9,016,545 B2 4/2015 Aranyi et al.
9,055,961 B2 6/2015 Manzo et al.
9,161,807 B2 10/2015 Garrison
9,192,378 B2 11/2015 Aranyi et al.
9,192,379 B2 11/2015 Aranyi et al.
9,211,120 B2 12/2015 Scheib et al.
9,216,019 B2 12/2015 Schmid et al.
9,307,986 B2 4/2016 Hall et al.
9,316,267 B2 4/2016 Lenz et al.
9,345,479 B2 5/2016 Racenet et al.
9,498,215 B2 11/2016 Duque et al.
9,681,870 B2 6/2017 Baxter, III et al.
9,717,497 B2 8/2017 Zerkle et al.
9,717,498 B2 8/2017 Aranyi et al.
9,757,126 B2 9/2017 Cappola
9,777,459 B2 10/2017 Zuritis
9,808,246 B2 11/2017 Shelton, IV et al.
9,877,721 B2 1/2018 Schellin et al.
9,936,949 B2 4/2018 Measamer et al.
10,111,659 B2 10/2018 Racenet et al.
10,130,367 B2 11/2018 Cappola et al.
10,231,732 B1 3/2019 Racenet et al.
10,231,733 B2 3/2019 Ehrenfels et al.
10,285,693 B2 5/2019 Kimsey et al.
D850,617 S 6/2019 Shelton, IV et al.
10,335,147 B2 7/2019 Rector et al.
10,363,037 B2 7/2019 Aronhalt et al.
10,383,628 B2 8/2019 Kang et al.
10,646,219 B2 5/2020 Racenet et al.
10,722,233 B2 7/2020 Wellman
10,828,027 B2 11/2020 Racenet et al.
10,863,988 B2 12/2020 Patel et al.
10,912,556 B2 2/2021 Burbank
10,973,517 B2 4/2021 Wixey
11,014,224 B2 5/2021 Dey, IV et al.
11,020,138 B2 6/2021 Ragosta
11,166,773 B2 11/2021 Ragosta et al.
11,185,331 B2 11/2021 Adams et al.
11,191,542 B2 12/2021 Miller et al.
11,234,700 B2 2/2022 Ragosta et al.
11,266,409 B2 3/2022 Huitema et al.
11,291,445 B2 4/2022 Shelton, IV et al.
11,439,390 B2 9/2022 Patel et al.
D967,421 S 10/2022 Shelton, IV et al.
11,504,124 B2 11/2022 Patel et al.
11,517,312 B2 12/2022 Wixey
11,607,219 B2 3/2023 Shelton, IV et al.
11,642,129 B2 5/2023 Burbank
11,696,758 B2 7/2023 Murphy et al.
11,723,661 B2 8/2023 Wixey et al.
11,759,202 B2 9/2023 Morgan et al.
11,786,325 B2 10/2023 Mustufa et al.
11,806,015 B2 11/2023 Wixey et al.
11,857,188 B2 1/2024 Hites
11,864,762 B2 1/2024 Wixey
11,896,224 B2 * 2/2024 Wellman .......... A61B 17/07207
11,903,583 B2 2/2024 Burbank et al.
11,944,301 B2 4/2024 Wixey et al.
11,944,302 B2 4/2024 Wixey et al.
11,986,184 B2 5/2024 Patel et al.
12,000,280 B2 6/2024 King
12,011,168 B2 6/2024 Wixey
D1,035,874 S 7/2024 Sun et al.
12,029,426 B2 7/2024 Millman et al.
12,029,473 B2 7/2024 Whitlock et al.
12,089,844 B2 9/2024 Patel et al.
12,137,903 B2 11/2024 Patel et al.
12,156,654 B2 12/2024 Wellman
D1,067,431 S 3/2025 Schings et al.
12,251,107 B2 3/2025 Wixey et al.
D1,070,086 S 4/2025 Yang et al.
12,262,891 B2 4/2025 Burbank
12,303,130 B2 5/2025 Wixey et al.
12,324,589 B2 6/2025 Kerver et al.
12,349,905 B2 * 7/2025 Wellman .......... A61B 17/07207
12,359,696 B2 7/2025 Wixey
12,383,268 B2 8/2025 Wixey et al.
12,402,883 B2 9/2025 Yee et al.
D1,097,151 S 10/2025 Sun et al.

(56) References Cited

U.S. PATENT DOCUMENTS

| | | | |
|---|---|---|---|
| 12,508,024 | B2 | 12/2025 | Jasemian et al. |
| 12,527,574 | B2 | 1/2026 | Hites |
| 2002/0165562 | A1 | 11/2002 | Grant et al. |
| 2002/0188293 | A1 | 12/2002 | Manzo |
| 2002/0188294 | A1 | 12/2002 | Couture et al. |
| 2003/0078577 | A1 | 4/2003 | Truckai et al. |
| 2003/0135204 | A1 | 7/2003 | Lee et al. |
| 2003/0135205 | A1 | 7/2003 | Davenport et al. |
| 2003/0144652 | A1 | 7/2003 | Baker et al. |
| 2003/0171747 | A1 | 9/2003 | Kanehira et al. |
| 2003/0181910 | A1 | 9/2003 | Dycus et al. |
| 2004/0006340 | A1 | 1/2004 | Latterell et al. |
| 2004/0049185 | A1 | 3/2004 | Latterell et al. |
| 2004/0143263 | A1 | 7/2004 | Schechter et al. |
| 2004/0232199 | A1 | 11/2004 | Shelton et al. |
| 2004/0267310 | A1 | 12/2004 | Racenet et al. |
| 2005/0006430 | A1 | 1/2005 | Wales |
| 2005/0006434 | A1 | 1/2005 | Wales et al. |
| 2005/0021027 | A1 | 1/2005 | Shields et al. |
| 2005/0070925 | A1 | 3/2005 | Shelton, IV et al. |
| 2005/0070958 | A1 | 3/2005 | Swayze et al. |
| 2005/0101991 | A1 | 5/2005 | Ahlberg et al. |
| 2005/0113826 | A1 | 5/2005 | Johnson et al. |
| 2005/0171533 | A1 | 8/2005 | Latterell et al. |
| 2005/0178813 | A1 | 8/2005 | Swayze et al. |
| 2005/0187576 | A1 | 8/2005 | Whitman et al. |
| 2005/0273084 | A1 | 12/2005 | Hinman et al. |
| 2005/0273085 | A1 | 12/2005 | Hinman et al. |
| 2006/0000868 | A1 | 1/2006 | Shelton, IV et al. |
| 2006/0016853 | A1 | 1/2006 | Racenet |
| 2006/0020287 | A1 | 1/2006 | Lee et al. |
| 2006/0022014 | A1 | 2/2006 | Shelton, IV et al. |
| 2006/0022015 | A1 | 2/2006 | Shelton, IV et al. |
| 2006/0024817 | A1 | 2/2006 | Deguchi et al. |
| 2006/0025809 | A1 | 2/2006 | Shelton, IV |
| 2006/0025810 | A1 | 2/2006 | Shelton, IV |
| 2006/0025811 | A1 | 2/2006 | Shelton, IV |
| 2006/0025812 | A1 | 2/2006 | Shelton, IV |
| 2006/0025813 | A1 | 2/2006 | Shelton et al. |
| 2006/0025816 | A1 | 2/2006 | Shelton, IV |
| 2006/0049230 | A1 | 3/2006 | Shelton, IV et al. |
| 2006/0097026 | A1 | 5/2006 | Shelton, IV |
| 2006/0111209 | A1 | 5/2006 | Hinman et al. |
| 2006/0111210 | A1 | 5/2006 | Hinman |
| 2006/0124689 | A1 | 6/2006 | Arad et al. |
| 2006/0161190 | A1 | 7/2006 | Gadberry et al. |
| 2006/0190031 | A1 | 8/2006 | Wales et al. |
| 2006/0199999 | A1 | 9/2006 | Ikeda et al. |
| 2006/0217706 | A1 | 9/2006 | Lau et al. |
| 2006/0217709 | A1 | 9/2006 | Couture et al. |
| 2006/0271042 | A1 | 11/2006 | Latterell et al. |
| 2007/0010838 | A1 | 1/2007 | Shelton, IV et al. |
| 2007/0045379 | A1 | 3/2007 | Shelton, IV |
| 2007/0250113 | A1 | 10/2007 | Hegeman et al. |
| 2007/0262116 | A1 | 11/2007 | Hueil et al. |
| 2007/0270884 | A1 | 11/2007 | Smith et al. |
| 2008/0023522 | A1 | 1/2008 | Olson et al. |
| 2008/0029577 | A1 | 2/2008 | Shelton et al. |
| 2008/0064572 | A1 | 3/2008 | Nardone |
| 2008/0065100 | A1 | 3/2008 | Larkin |
| 2008/0078804 | A1 | 4/2008 | Shelton et al. |
| 2008/0086114 | A1 | 4/2008 | Schmitz et al. |
| 2008/0093517 | A1 | 4/2008 | Chen |
| 2008/0108446 | A1 | 5/2008 | Faude |
| 2008/0161174 | A1 | 7/2008 | Lo |
| 2008/0196533 | A1 | 8/2008 | Bergamasco et al. |
| 2008/0210738 | A1 | 9/2008 | Shelton et al. |
| 2008/0280736 | A1 | 11/2008 | D'Eredita |
| 2008/0305934 | A1 | 12/2008 | Medina |
| 2008/0308607 | A1 | 12/2008 | Timm et al. |
| 2009/0090763 | A1 | 4/2009 | Zemlok et al. |
| 2009/0181832 | A1 | 7/2009 | Bell |
| 2009/0277947 | A1 | 11/2009 | Viola |
| 2010/0006620 | A1 | 1/2010 | Sorrentino et al. |
| 2010/0009818 | A1 | 1/2010 | Simonson et al. |
| 2010/0057081 | A1 | 3/2010 | Hanna |
| 2010/0057085 | A1 | 3/2010 | Holcomb et al. |
| 2010/0076461 | A1 | 3/2010 | Viola et al. |
| 2010/0076474 | A1 | 3/2010 | Yates et al. |
| 2010/0096431 | A1 | 4/2010 | Smith et al. |
| 2010/0108740 | A1 | 5/2010 | Pastorelli et al. |
| 2010/0145334 | A1 | 6/2010 | Olson et al. |
| 2010/0179545 | A1 | 7/2010 | Twomey et al. |
| 2010/0198248 | A1 | 8/2010 | Vakharia |
| 2010/0213240 | A1 | 8/2010 | Kostrzewski |
| 2010/0331857 | A1 | 12/2010 | Doyle et al. |
| 2011/0011915 | A1 | 1/2011 | Shelton, IV |
| 2011/0017801 | A1 | 1/2011 | Zemlok et al. |
| 2011/0022078 | A1 | 1/2011 | Hinman |
| 2011/0036891 | A1 | 2/2011 | Zemlok et al. |
| 2011/0042439 | A1 | 2/2011 | Johnson et al. |
| 2011/0087238 | A1 | 4/2011 | Wang et al. |
| 2011/0118707 | A1 | 5/2011 | Burbank |
| 2011/0121049 | A1 | 5/2011 | Malinouskas et al. |
| 2011/0121050 | A1 | 5/2011 | Nicholas et al. |
| 2011/0139851 | A1 | 6/2011 | Mccuen |
| 2011/0152879 | A1 | 6/2011 | Williams |
| 2011/0174863 | A1 | 7/2011 | Shelton, IV et al. |
| 2011/0186614 | A1 | 8/2011 | Kasvikis |
| 2011/0204119 | A1 | 8/2011 | McCuen |
| 2011/0251613 | A1 | 10/2011 | Guerra et al. |
| 2011/0282339 | A1 | 11/2011 | Weizman et al. |
| 2011/0288573 | A1 | 11/2011 | Yates et al. |
| 2011/0290851 | A1 | 12/2011 | Shelton, IV |
| 2011/0290853 | A1 | 12/2011 | Shelton, IV et al. |
| 2011/0290854 | A1 | 12/2011 | Timm et al. |
| 2011/0290855 | A1 | 12/2011 | Moore et al. |
| 2011/0295269 | A1 | 12/2011 | Swensgard et al. |
| 2011/0295270 | A1 | 12/2011 | Giordano et al. |
| 2011/0301603 | A1 | 12/2011 | Kerr et al. |
| 2011/0319886 | A1 | 12/2011 | Chojin et al. |
| 2012/0000962 | A1 | 1/2012 | Racenet et al. |
| 2012/0022584 | A1 | 1/2012 | Donnigan et al. |
| 2012/0071891 | A1 | 3/2012 | Itkowitz et al. |
| 2012/0205419 | A1 | 8/2012 | Weir et al. |
| 2012/0209253 | A1 | 8/2012 | Donhowe |
| 2012/0223121 | A1 | 9/2012 | Viola et al. |
| 2012/0228358 | A1 | 9/2012 | Zemlok et al. |
| 2012/0248167 | A1 | 10/2012 | Flanagan et al. |
| 2012/0255986 | A1 | 10/2012 | Petty et al. |
| 2012/0265241 | A1 | 10/2012 | Hart et al. |
| 2012/0289999 | A1 | 11/2012 | Frank |
| 2012/0298719 | A1 | 11/2012 | Shelton, IV et al. |
| 2013/0015231 | A1 | 1/2013 | Kostrzewski |
| 2013/0037597 | A1 | 2/2013 | Katre et al. |
| 2013/0046303 | A1 | 2/2013 | Evans et al. |
| 2013/0056521 | A1 | 3/2013 | Swensgard |
| 2013/0068821 | A1 | 3/2013 | Huitema et al. |
| 2013/0075448 | A1 | 3/2013 | Schmid et al. |
| 2013/0087599 | A1 | 4/2013 | Krumanaker et al. |
| 2013/0098965 | A1 | 4/2013 | Kostrzewski et al. |
| 2013/0098966 | A1 | 4/2013 | Kostrzewski et al. |
| 2013/0116668 | A1 | 5/2013 | Shelton, IV et al. |
| 2013/0126586 | A1 | 5/2013 | Zhang et al. |
| 2013/0148577 | A1 | 6/2013 | Terry et al. |
| 2013/0240604 | A1 | 9/2013 | Knodel |
| 2013/0248577 | A1 | 9/2013 | Leimbach et al. |
| 2013/0256373 | A1 | 10/2013 | Schmid et al. |
| 2013/0277410 | A1 | 10/2013 | Fernandez et al. |
| 2013/0282052 | A1 | 10/2013 | Aranyi et al. |
| 2013/0296922 | A1 | 11/2013 | Allen, IV et al. |
| 2013/0327808 | A1 | 12/2013 | Chen et al. |
| 2013/0327809 | A1 | 12/2013 | Shelton, IV et al. |
| 2014/0001236 | A1 | 1/2014 | Shelton, IV et al. |
| 2014/0005653 | A1 | 1/2014 | Shelton, IV et al. |
| 2014/0005654 | A1 | 1/2014 | Batross et al. |
| 2014/0005662 | A1 | 1/2014 | Shelton, IV |
| 2014/0005677 | A1 | 1/2014 | Shelton, IV et al. |
| 2014/0021239 | A1 | 1/2014 | Kostrzewski |
| 2014/0025071 | A1 | 1/2014 | Sims et al. |
| 2014/0027492 | A1 | 1/2014 | Williams |
| 2014/0100569 | A1 | 4/2014 | Lawes et al. |
| 2014/0100600 | A1 | 4/2014 | Kendrick |
| 2014/0103093 | A1 | 4/2014 | Koch, Jr. et al. |

(56) References Cited

U.S. PATENT DOCUMENTS

2014/0110455 A1 4/2014 Ingmanson et al.
2014/0128867 A1 5/2014 Collings et al.
2014/0131418 A1 5/2014 Kostrzewski
2014/0175152 A1 6/2014 Hess et al.
2014/0180286 A1 6/2014 Marczyk et al.
2014/0200596 A1 7/2014 Weir et al.
2014/0200612 A1 7/2014 Weir et al.
2014/0200851 A1 7/2014 Weir et al.
2014/0214049 A1 7/2014 Jeong et al.
2014/0239036 A1 8/2014 Zerkle et al.
2014/0239044 A1 8/2014 Hoffman
2014/0239046 A1 8/2014 Milliman et al.
2014/0246477 A1 9/2014 Koch, Jr. et al.
2014/0249557 A1 9/2014 Koch, Jr. et al.
2014/0257331 A1 9/2014 Kim et al.
2014/0263546 A1 9/2014 Aranyi
2014/0263552 A1 9/2014 Hall et al.
2014/0263559 A1 9/2014 Williams et al.
2014/0263565 A1 9/2014 Lytle, IV et al.
2014/0263567 A1 9/2014 Williams et al.
2014/0263569 A1 9/2014 Williams et al.
2014/0276731 A1 9/2014 Voegele et al.
2014/0276776 A1 9/2014 Parihar et al.
2014/0284372 A1 9/2014 Kostrzewski
2014/0305989 A1 10/2014 Parihar et al.
2014/0309666 A1 10/2014 Shelton, IV et al.
2014/0343550 A1 11/2014 Faller et al.
2014/0343569 A1 11/2014 Turner
2014/0345971 A1 11/2014 Norris
2014/0364851 A1 12/2014 Batross et al.
2015/0018856 A1 1/2015 Poo et al.
2015/0073746 A1 3/2015 Gris et al.
2015/0088131 A1 3/2015 Weisshaupt et al.
2015/0141981 A1 5/2015 Price et al.
2015/0141993 A1 5/2015 Schechter et al.
2015/0173756 A1 6/2015 Baxter, III et al.
2015/0173789 A1 6/2015 Baxter, III et al.
2015/0209030 A1 7/2015 Kostrzewski et al.
2015/0209037 A1 7/2015 Kostrzewski et al.
2015/0250530 A1 9/2015 Manzo et al.
2015/0256609 A1 9/2015 Morton et al.
2015/0272575 A1 10/2015 Leimbach et al.
2015/0272583 A1 10/2015 Leimbach et al.
2015/0272606 A1 10/2015 Nobis
2015/0297227 A1 10/2015 Huitema et al.
2015/0297235 A1 10/2015 Harris et al.
2015/0316431 A1 11/2015 Collins et al.
2015/0369277 A1 12/2015 Fevre et al.
2015/0374396 A1 12/2015 Strobl et al.
2016/0038227 A1 2/2016 Garrison
2016/0058441 A1 3/2016 Morgan et al.
2016/0058450 A1 3/2016 Shelton, IV et al.
2016/0066916 A1 3/2016 Overmyer et al.
2016/0089148 A1 3/2016 Harris et al.
2016/0120544 A1 5/2016 Shelton, IV et al.
2016/0157863 A1 6/2016 Williams et al.
2016/0157926 A1 6/2016 Boudreaux
2016/0166256 A1 6/2016 Baxter, III et al.
2016/0174973 A1 6/2016 Shelton, IV et al.
2016/0174977 A1 6/2016 Lytle, IV et al.
2016/0175033 A1 6/2016 Le
2016/0192999 A1 7/2016 Stulen et al.
2016/0199124 A1 7/2016 Thomas et al.
2016/0235473 A1 8/2016 Hagland
2016/0235489 A1 8/2016 Gombert et al.
2016/0242782 A1 8/2016 Shelton, IV et al.
2016/0249921 A1 9/2016 Cappola et al.
2016/0270780 A1 9/2016 Hall et al.
2016/0287251 A1 10/2016 Shelton, IV et al.
2016/0287316 A1 10/2016 Worrell et al.
2016/0296226 A1 10/2016 Kostrzewski
2016/0317216 A1 11/2016 Hermes et al.
2016/0338764 A1 11/2016 Krastins et al.
2016/0345971 A1 12/2016 Bucciaglia et al.
2016/0374672 A1 12/2016 Bear et al.
2016/0374673 A1 12/2016 Stager et al.
2017/0010578 A1 1/2017 Miyakawa
2017/0042604 A1 2/2017 McFarland et al.
2017/0055981 A1 3/2017 Vendely et al.
2017/0056098 A1 3/2017 Crews et al.
2017/0065331 A1 3/2017 Mayer et al.
2017/0079710 A1 3/2017 Deville et al.
2017/0097035 A1 4/2017 Zimmerman et al.
2017/0105754 A1 4/2017 Boudreaux et al.
2017/0135746 A1 5/2017 Tetzlaff et al.
2017/0143335 A1 5/2017 Gupta et al.
2017/0156788 A1 6/2017 Johnson et al.
2017/0189028 A1 7/2017 Aranyi
2017/0202605 A1 7/2017 Shelton, IV et al.
2017/0231653 A1 8/2017 Kapadia
2017/0245857 A1 8/2017 Shelton, IV et al.
2017/0265865 A1 9/2017 Burbank
2017/0290584 A1 10/2017 Jasemian et al.
2017/0296172 A1 10/2017 Harris et al.
2017/0296173 A1 10/2017 Shelton, IV et al.
2017/0296183 A1 10/2017 Shelton, IV et al.
2018/0008265 A1 1/2018 Hatanaka et al.
2018/0021042 A1 1/2018 Nicholas et al.
2018/0078268 A1 3/2018 Messerly et al.
2018/0125570 A1 5/2018 Rioux
2018/0161052 A1 6/2018 Weir et al.
2018/0168581 A1 6/2018 Hunter et al.
2018/0168585 A1 6/2018 Shelton, IV et al.
2018/0168607 A1 6/2018 Shelton, IV et al.
2018/0168620 A1 6/2018 Huang et al.
2018/0168622 A1 6/2018 Shelton, IV et al.
2018/0168628 A1 6/2018 Hunter et al.
2018/0168637 A1 6/2018 Harris et al.
2018/0168641 A1 6/2018 Harris et al.
2018/0168642 A1 6/2018 Shelton, IV et al.
2018/0168644 A1 6/2018 Shelton, IV et al.
2018/0168649 A1 6/2018 Shelton, IV et al.
2018/0168650 A1 6/2018 Shelton, IV et al.
2018/0206844 A1 7/2018 Harris et al.
2018/0214200 A1 8/2018 Nanditale et al.
2018/0232951 A1 8/2018 Alterovitz et al.
2018/0250085 A1 9/2018 Simi et al.
2018/0296213 A1 10/2018 Strobl
2018/0310948 A1 11/2018 Stamm et al.
2018/0317915 A1 11/2018 McDonald, II
2018/0353186 A1 12/2018 Mozdzierz et al.
2019/0000454 A1 1/2019 Swayze et al.
2019/0000525 A1 1/2019 Messerly et al.
2019/0015124 A1 1/2019 Williams et al.
2019/0029746 A1 1/2019 Dudhedia et al.
2019/0059894 A1 2/2019 Kumada et al.
2019/0076143 A1 3/2019 Smith
2019/0083086 A1 3/2019 Klaffenböck et al.
2019/0083819 A1 3/2019 Mitchell et al.
2019/0099181 A1 4/2019 Shelton, IV et al.
2019/0125347 A1 5/2019 Stokes et al.
2019/0133571 A1 5/2019 Racenet et al.
2019/0142531 A1 5/2019 Wentworth et al.
2019/0150919 A1 5/2019 Williams et al.
2019/0192137 A1 6/2019 Shelton, IV et al.
2019/0201146 A1 7/2019 Shelton, IV et al.
2019/0231350 A1 8/2019 Scott et al.
2019/0239881 A1 8/2019 Laurent et al.
2019/0282233 A1 9/2019 Burbank et al.
2019/0290374 A1 9/2019 Ramadorai
2019/0298346 A1 10/2019 Shelton, IV et al.
2019/0298354 A1 10/2019 Shelton, IV et al.
2019/0298355 A1 10/2019 Shelton, IV et al.
2019/0298356 A1 10/2019 Shelton, IV et al.
2019/0314107 A1 10/2019 Worrell et al.
2020/0054338 A1 2/2020 Shen
2020/0205811 A1 7/2020 Posey et al.
2020/0214706 A1 7/2020 Vendely et al.
2020/0305872 A1 10/2020 Weidner et al.
2021/0059670 A1 3/2021 Overmyer et al.
2021/0153927 A1 5/2021 Ross et al.
2021/0177412 A1 6/2021 Wilson et al.
2021/0177495 A1 6/2021 Ross et al.
2021/0177500 A1 6/2021 Khalaji

(56) References Cited

U.S. PATENT DOCUMENTS

| | | | |
|---|---|---|---|
| 2021/0186494 | A1 | 6/2021 | Shelton, IV et al. |
| 2021/0196350 | A1 | 7/2021 | Fiebig et al. |
| 2021/0236119 | A1 | 8/2021 | Chavan et al. |
| 2021/0267596 | A1 | 9/2021 | Fanelli et al. |
| 2021/0290232 | A1 | 9/2021 | Harris et al. |
| 2021/0290233 | A1 | 9/2021 | Shelton, IV et al. |
| 2022/0015823 | A1 | 1/2022 | Wilson et al. |
| 2022/0031346 | A1 | 2/2022 | Parks |
| 2022/0054130 | A1 | 2/2022 | Overmyer et al. |
| 2022/0061836 | A1 | 3/2022 | Parihar et al. |
| 2022/0079585 | A1 | 3/2022 | Egan |
| 2022/0125428 | A1 | 4/2022 | Ragosta et al. |
| 2022/0142642 | A1 | 5/2022 | De Maillé et al. |
| 2022/0167985 | A1 | 6/2022 | George et al. |
| 2022/0218344 | A1 | 7/2022 | Leimbach et al. |
| 2022/0296243 | A1 | 9/2022 | Nalagatla et al. |
| 2022/0304691 | A1 | 9/2022 | Fernandes et al. |
| 2022/0378537 | A1 | 12/2022 | Hites et al. |
| 2022/0387027 | A1 | 12/2022 | Shelton, IV et al. |
| 2023/0099430 | A1 | 3/2023 | Schings et al. |
| 2023/0101993 | A1 | 3/2023 | Baril et al. |
| 2023/0120209 | A1 | 4/2023 | Parks et al. |
| 2023/0121658 | A1 | 4/2023 | Stokes et al. |
| 2023/0210527 | A1 | 7/2023 | Shelton, IV et al. |
| 2023/0329711 | A1 | 10/2023 | Wixey et al. |
| 2024/0065690 | A1 | 2/2024 | Jasemian et al. |
| 2024/0081824 | A1 | 3/2024 | Hites |
| 2024/0108343 | A1 | 4/2024 | Wixey |
| 2024/0188956 | A1 | 6/2024 | Swayze et al. |
| 2024/0252171 | A1 | 8/2024 | Wixey et al. |
| 2024/0293122 | A1 | 9/2024 | Wixey |
| 2024/0315761 | A1 | 9/2024 | Whitlock et al. |
| 2024/0335194 | A1 | 10/2024 | Patel et al. |
| 2024/0341766 | A1 | 10/2024 | Millman et al. |
| 2024/0350143 | A1 | 10/2024 | Yee et al. |
| 2024/0407782 | A1 | 12/2024 | Patel et al. |
| 2025/0040930 | A1 | 2/2025 | Wellman |
| 2025/0261940 | A1 | 8/2025 | Wixey et al. |
| 2025/0302472 | A1 | 10/2025 | Wixey et al. |
| 2025/0325275 | A1 | 10/2025 | Kerver |
| 2025/0331857 | A1 | 10/2025 | Wixey et al. |
| 2025/0359870 | A1 | 11/2025 | Yee et al. |
| 2026/0020899 | A1 | 1/2026 | Khalaji |

FOREIGN PATENT DOCUMENTS

| | | | |
|---|---|---|---|
| CN | 104042275 | A | 9/2014 |
| CN | 105007836 | A | 10/2015 |
| CN | 105769331 | A | 7/2016 |
| CN | 106232026 | A | 12/2016 |
| CN | 106491203 | A | 3/2017 |
| CN | 107920819 | A | 4/2018 |
| CN | 108024809 | A | 5/2018 |
| CN | 112165909 | A | 1/2021 |
| DE | 694747 | C | 8/1940 |
| DE | 3724525 | C1 | 5/1988 |
| DE | 102012103503 | A1 | 10/2013 |
| EP | 0277532 | B1 | 8/1990 |
| EP | 0469396 | A1 | 2/1992 |
| EP | 0277529 | B1 | 4/1993 |
| EP | 0641546 | A1 | 3/1995 |
| EP | 0986336 | A1 | 3/2000 |
| EP | 1090592 | A1 | 4/2001 |
| EP | 1479348 | A1 | 11/2004 |
| EP | 1728473 | A1 | 12/2006 |
| EP | 1479346 | B1 | 1/2007 |
| EP | 1621141 | B1 | 7/2007 |
| EP | 2374419 | A2 | 10/2011 |
| EP | 1316290 | B1 | 2/2012 |
| EP | 2517639 | A1 | 10/2012 |
| EP | 2540231 | A2 | 1/2013 |
| EP | 1754445 | B1 | 10/2013 |
| EP | 2774548 | A2 | 9/2014 |
| EP | 2777529 | A1 | 9/2014 |
| EP | 2777530 | A1 | 9/2014 |
| EP | 2777532 | A2 | 9/2014 |
| EP | 2777535 | A1 | 9/2014 |
| EP | 2779921 | A2 | 9/2014 |
| EP | 2932918 | A1 | 10/2015 |
| EP | 2944275 | A2 | 11/2015 |
| EP | 2992849 | A1 | 3/2016 |
| EP | 3000408 | A2 | 3/2016 |
| EP | 3120780 | A2 | 1/2017 |
| EP | 3135225 | A2 | 3/2017 |
| EP | 3158947 | A1 | 4/2017 |
| EP | 3173029 | A1 | 5/2017 |
| EP | 3205291 | A1 | 8/2017 |
| EP | 3338703 | A1 | 6/2018 |
| EP | 2992834 | B1 | 12/2018 |
| EP | 3498190 | A1 | 6/2019 |
| EP | 3756567 | A1 | 12/2020 |
| FR | 2828952 | B1 | 12/2005 |
| JP | S5794132 | A | 6/1982 |
| JP | 2001170069 | A | 6/2001 |
| JP | 5301166 | B2 | 9/2013 |
| JP | 2014530653 | A | 11/2014 |
| JP | 2016508792 | A | 3/2016 |
| JP | 2016513570 | A | 5/2016 |
| JP | 2017500146 | A | 1/2017 |
| JP | 2017513564 | A | 6/2017 |
| JP | 2017527396 | A | 9/2017 |
| JP | 6411461 | B2 | 10/2018 |
| JP | 2019141659 | A | 8/2019 |
| KR | 20170060064 | A | 5/2017 |
| SU | 405234 | A1 | 9/1975 |
| SU | 886900 | A1 | 12/1981 |
| SU | 1333319 | A2 | 8/1987 |
| SU | 1442191 | A1 | 12/1988 |
| SU | 1459659 | A1 | 2/1989 |
| WO | WO-8602254 | A1 | 4/1986 |
| WO | WO-9005489 | A1 | 5/1990 |
| WO | WO-9734533 | A1 | 9/1997 |
| WO | WO-03094743 | A1 | 11/2003 |
| WO | WO-03094746 | A1 | 11/2003 |
| WO | WO-03094747 | A1 | 11/2003 |
| WO | WO-2004020859 | A1 | 3/2004 |
| WO | WO-2009112802 | A1 | 9/2009 |
| WO | WO-2012142872 | A1 | 10/2012 |
| WO | WO-2014106275 | A1 | 7/2014 |
| WO | WO-2016073538 | A1 | 5/2016 |
| WO | WO-2017026141 | A1 | 2/2017 |
| WO | WO-2017034803 | A2 | 3/2017 |
| WO | WO-2017156070 | A1 | 9/2017 |
| WO | WO-2017214243 | A1 | 12/2017 |
| WO | WO-2018005750 | A1 | 1/2018 |
| WO | WO-2018071497 | A1 | 4/2018 |
| WO | WO-2018118402 | A1 | 6/2018 |
| WO | WO-2019090047 | A1 | 5/2019 |
| WO | WO-2020081960 | A1 | 4/2020 |
| WO | WO-2020131685 | A1 | 6/2020 |
| WO | WO-2020131692 | A1 | 6/2020 |
| WO | WO-2022150215 | A1 | 7/2022 |
| WO | WO-2022200951 | A1 | 9/2022 |

OTHER PUBLICATIONS

Burstein M.D., "8 MM Sureform 30 Staplers and Reloads," Sages, Jun. 2022, 1 Page. Retrieved from internet URL: https://www.accessdata.fda.gov/cdrh_docs/pdf21/K211997.pdf.

European Search Report (Corrected version) for Application No. EP19750317.0, mailed on Mar. 28, 2022, 26 pages.

Extended European Search Report for Application No. EP18823002.3 mailed on Mar. 5, 2021,11 pages.

Extended European Search Report for Application No. EP19757451.0, mailed on May 19, 2022, 16 pages.

Extended European Search Report for Application No. EP19898247.2, mailed on Jan. 10, 2023, 12 pages.

Extended European Search Report for Application No. EP19900059.7, mailed on Dec. 5, 2022, 10 pages.

Extended European Search Report for Application No. EP20790773.4, mailed on Nov. 29, 2022, 09 pages.

Extended European Search Report for Application No. EP20815112.6, mailed on Jan. 5, 2023, 11 pages.

(56) References Cited

OTHER PUBLICATIONS

Extended European Search Report for Application No. EP20875978.7, mailed on Jan. 31, 2024, 26 pages.
Extended European Search Report for Application No. EP24155564.8, mailed on Jul. 8, 2024, 12 pages.
Field Application Note—Journal Bearings, Retrieved from Wayback Machine URL: https://web.archive.org/web/20100110095051/ http://www.reliabilitydirect.com/appnotes/jb.html, on Mar. 12, 2024, 04 pages.
International Preliminary Report on Patentability for Application No. PCT/US2019/017646, mailed on Aug. 27, 2020, 10 pages.
International Preliminary Report on Patentability for Application No. PCT/US2019/019501, mailed Sep. 3, 2020, 7 pages.
International Search Report and Written Opinion for Application No. PCT/US19/17646, mailed on Apr. 16, 2019, 11 pages.
International Search Report and Written Opinion for Application No. PCT/US2016/059527, mailed on Feb. 16, 2017, 13 pages.
International Search Report and Written Opinion for Application No. PCT/US2018/039912, mailed on Oct. 12, 2018, 15 pages.
International Search Report and Written Opinion for Application No. PCT/US2019/019501, mailed May 9, 2019, 8 pages.
International Search Report and Written Opinion for Application No. PCT/US2019/056979, mailed Dec. 18, 2019, 8 pages.
International Search Report and Written Opinion for Application No. PCT/US2019/062344, mailed Mar. 23, 2020, 17 pages.
International Search Report and Written Opinion for Application No. PCT/US2019/062768, mailed Mar. 9, 2020, 15 pages.
International Search Report and Written Opinion for Application No. PCT/US2019/064861, mailed Mar. 30, 2020, 18 pages.
International Search Report and Written Opinion for Application No. PCT/US2019/066513, mailed Apr. 21, 2020, 8 pages.
International Search Report and Written Opinion for Application No. PCT/US2019/066530, mailed Apr. 21, 2020, 8 pages.
International Search Report and Written Opinion for Application No. PCT/US2021/065544 mailed Jun. 2, 2022, 21 pages.
International Search Report and Written Opinion for Application No. PCT/US2020/020672, mailed Jun. 29, 2020, 10 pages.
International Search Report and Written Opinion for Application No. PCT/US2020/025655, mailed Jul. 22, 2020, 8 pages.
International Search Report and Written Opinion for Application No. PCT/US2020/033481, mailed Sep. 3, 2020, 22 pages.
International Search Report and Written Opinion for Application No. PCT/US2020/054568, mailed Jan. 29, 2021, 13 pages.
International Search Report and Written Opinion for Application No. PCT/US2021/012284 mailed May 6, 2021,23 pages.
International Search Report and Written Opinion for Application No. PCT/US2021/065308, mailed Apr. 21, 2022, 13 pages.
International Search Report and Written Opinion for Application No. PCT/US2024/026826, mailed Jul. 26, 2024, 15 pages.
Jaggi A., "8 mm SureForm 30 Curved-Tip Stapler, 8 mm SureForm 30 Stapler, SureForm 30 Reloads," U.S Food & Drug Administration, Dec. 2021, 11 pages. Retrieved from the internet URL:https://www.sages.org/publications/tavac/8-mm-sureform-30-staplers-and-reloads/.
Nicholson, C., et al., "Plane Bearings," ESC Report, BSA Educational Services Committee, Oct. 1994, vol. 5(1), 02 pages.
Partial European Search Report for Application No. EP19757451.0, mailed on Feb. 2, 2022, 12 pages.
Supplementary European Search Report for Application No. EP19873128.3, mailed on Jun. 22, 2022, 7 pages.
Vertut, J., and Coiffet, P., "Robot Technology: Teleoperation and Robotics Evolution and Development," English translation, Prentice-Hall, Inc., Inglewood Cliffs, NJ, USA 1986, vol. 3A, 332 pages.
Article Name, found online xx/xx/xxxx at amazon.com (store brand base url). Reference dated xx/xx/xxxx. Retrieved from https://web.archive.org/web/20140704001512/ http://www.adorama.com/FSSTC10.html.
"Echelon Gripping Surface Technology Reloads," Ethicon, 2023, 1 Page. Retrieved from online URL:[https://web.archive.Org/web/20230328053734/https://www.jnjmedtech.com/en-US/product/ echelon-gripping-surfacetechnology reloads].
"Itoya ⅜" Switch Heavy Duty Disposable Staple Cassettes," Adorama, 2014, 1 page. Retrieved from Online URL: [https://web.archive.Org/web/20140704001512/ http://www.adorama.com/FSSTC10.html].
"Linear Cutter Stapler," Fengh Europe, 2024, 1 Page. Retrieved from Online URL: [https://web.archive.org/web/20240223162323/https://fenghmedical.nl/product/linear-cutter-stapler/].
McKesson Staple Loading Unit, found online Dec. 30, 2025 at https://mms.mckesson.comReference dated Apr. 15, 2021. Retrieved fromhttps://web.archive.Org/web/20210415093906/https://mms.mckesson.com/product/453729/ J-J-Healthcare-Systems-6R45B.

* cited by examiner

STAPLE CARTRIDGE FOR A SURGICAL INSTRUMENT

CROSS-REFERENCE TO RELATED APPLICATIONS

This application is a continuation of U.S. patent application Ser. No. 18/406,333 filed Jan. 8, 2024, which is a Continuation of U.S. patent application Ser. No. 17/605,230 filed Oct. 20, 2021, Issued as U.S. Pat. No. 11,896,224 on Feb. 13, 2024, which is a U.S. National Stage application of PCT/US20/33481 filed on May 18, 2020 which claims the benefit of U.S. Provisional Application Ser. No. 62/855,371, filed May 31, 2019, the entire disclosure of each are incorporated herein by reference for all purposes.

BACKGROUND

The field of the present disclosure relates to medical instruments, and more particularly to tissue sealing instruments for use in surgeries. Even more particularly, the present disclosure relates to a surgical stapling instrument having a more compact staple cartridge for holding a staple.

Minimally invasive medical techniques are intended to reduce the amount of extraneous tissue that is damaged during diagnostic or surgical procedures, thereby reducing patient recovery time, discomfort, and deleterious side effects. One effect of minimally invasive surgery, for example, is reduced post-operative hospital recovery times. The average hospital stay for a standard open surgery is typically significantly longer than the average stay for an analogous minimally invasive surgery (MIS). Thus, increased use of MIS could save millions of dollars in hospital costs each year. While many of the surgeries performed each year in the United States could potentially be performed in a minimally invasive manner, only a portion of the current surgeries uses these advantageous techniques due to limitations in minimally invasive surgical instruments and the additional surgical training involved in mastering them.

Improved surgical instruments such as tissue access, navigation, dissection and sealing instruments have enabled MIS to redefine the field of surgery. These instruments allow surgeries and diagnostic procedures to be performed with reduced trauma to the patient. A common form of minimally invasive surgery is endoscopy, and a common form of endoscopy is laparoscopy, which is minimally invasive inspection and surgery inside the abdominal cavity. In standard laparoscopic surgery, a patient's abdomen is insufflated with gas, and cannula sleeves are passed through small (approximately one-half inch or less) incisions to provide entry ports for laparoscopic instruments.

Laparoscopic surgical instruments generally include an endoscope (e.g., laparoscope) for viewing the surgical field and tools for working at the surgical site. The working tools are typically similar to those used in conventional (open) surgery, except that the working end or end effector of each tool is separated from its handle by an extension tube (also known as, e.g., an instrument shaft or a main shaft). The end effector can include, for example, a clamp, grasper, scissor, stapler, cautery tool, linear cutter, or needle holder.

To perform surgical procedures, the surgeon passes working tools through cannula sleeves to an internal surgical site and manipulates them from outside the abdomen. The surgeon views the procedure from a monitor that displays an image of the surgical site taken from the endoscope. Similar endoscopic techniques are employed in, for example, arthroscopy, retroperitoneoscopy, pelviscopy, nephroscopy, cystoscopy, cisternoscopy, sinoscopy, hysteroscopy, uretbroscopy, and the like.

Minimally invasive telesurgical robotic systems are being developed to increase a surgeon's dexterity when working on an internal surgical site, as well as to allow a surgeon to operate on a patient from a remote location (outside the sterile field). In a telesurgery system, the surgeon is often provided with an image of the surgical site at a control console. While viewing a three dimensional image of the surgical site on a suitable viewer or display, the surgeon performs the surgical procedures on the patient by manipulating master input or control devices of the control console, which in turn control motion of the servo-mechanically operated slave instruments.

The servomechanism used for telesurgery will often accept input from two master controllers (one for each of the surgeon's hands) and may include two or more robotic arms on each of which a surgical instrument is mounted. Operative communication between master controllers and associated robotic arm and instrument assemblies is typically achieved through a control system. The control system typically includes at least one processor that relays input commands from the master controllers to the associated robotic arm and instrument assemblies and back from the instrument and arm assemblies to the associated master controllers in the case of, for example, force feedback or the like. One example of a robotic surgical system is the DA VINCI™ system commercialized by Intuitive Surgical, Inc. of Sunnyvale, California.

A variety of structural arrangements have been used to support the surgical instrument at the surgical site during robotic surgery. The driven linkage or "slave" is often called a robotic surgical manipulator, and exemplary linkage arrangements for use as a robotic surgical manipulator during minimally invasive robotic surgery are described in U.S. Pat. No. 7,594,912 (filed Sep. 30, 2004), U.S. Pat. No. 6,758,843 (filed Apr. 26, 2002), U.S. Pat. No. 6,246,200 (filed Aug. 3, 1999), and U.S. Pat. No. 5,800,423 (filed Jul. 20, 1995), the full disclosures of which are incorporated herein by reference in their entirety for all purposes. These linkages often manipulate an instrument holder to which an instrument having a shaft is mounted. Such a manipulator structure can include a parallelogram linkage portion that generates motion of the instrument holder that is limited to rotation about a pitch axis that intersects a remote center of manipulation located along the length of the instrument shaft. Such a manipulator structure can also include a yaw joint that generates motion of the instrument holder that is limited to rotation about a yaw axis that is perpendicular to the pitch axis and that also intersects the remote center of manipulation. By aligning the remote center of manipulation with the incision point to the internal surgical site (for example, with a trocar or cannula at an abdominal wall during laparoscopic surgery), an end effector of the surgical instrument can be positioned safely by moving the proximal end of the shaft using the manipulator linkage without imposing potentially hazardous forces against the abdominal wall. Alternative manipulator structures are described, for example, in U.S. Pat. No. 6,702,805 (filed Nov. 9, 2000), U.S. Pat. No. 6,676,669 (filed Jan. 16, 2002), U.S. Pat. No. 5,855,583 (filed Nov. 22, 1996), U.S. Pat. No. 5,808,665 (filed Sep. 9, 1996), U.S. Pat. No. 5,445,166 (filed Apr. 6, 1994), and U.S. Pat. No. 5,184,601 (filed Aug. 5, 1991), the full disclosures of which are incorporated herein by reference in their entirety for all purposes.

During the surgical procedure, the telesurgical system can provide mechanical actuation and control of a variety of surgical instruments or tools having end effectors that perform various functions for the surgeon, for example, holding or driving a needle, grasping a blood vessel, dissecting tissue, or the like, in response to manipulation of the master input devices. Manipulation and control of these end effectors is a particularly beneficial aspect of robotic surgical systems. For this reason, it is desirable to provide surgical tools that include mechanisms that provide three degrees of rotational movement of an end effector to mimic the natural action of a surgeon's wrist. Such mechanisms should be appropriately sized for use in a minimally invasive procedure and relatively simple in design to reduce possible points of failure. In addition, such mechanisms should provide an adequate range of motion to allow the end effector to be manipulated in a wide variety of positions.

Surgical clamping and cutting instruments (e.g., non-robotic linear clamping, stapling, and cutting devices, also known as surgical staplers; and electrosurgical vessel sealing devices) have been employed in many different surgical procedures. For example, a surgical stapler can be used to resect a cancerous or anomalous tissue from a gastro-intestinal tract. Many known surgical clamping and cutting devices, including known surgical staplers, have opposing jaws that clamp tissue and an articulated knife to cut the clamped tissue.

Surgical clamping and cutting instruments are often deployed into restrictive body cavities (e.g., through a cannula to inside the pelvis). Accordingly, it is desirable for the surgical clamping and cutting instrument to be both compact and maneuverable for best access to and visibility of the surgical site. Known surgical clamping and cutting instruments, however, may fail to be both compact and maneuverable. For example, known surgical staplers may lack maneuverability with respect to multiple degrees of freedom (e.g., Roll, Pitch, and Yaw) and associated desired ranges of motion.

Conventional surgical clamping and cutting instruments often include a staple cartridge designed to fit within the movable jaw of the end effector. The staple cartridge typically contains multiple rows of staple assemblies that each includes a staple and a staple pusher. The staple pusher holds the staple in place prior to use, and then drives the staple into tissue when the instrument is actuated. The requisite size and shape of the staple cartridge, however, limits the ability of the designer to reduce the size and shape of the overall surgical instrument.

Surgical staples typically include two vertical legs connected by a backspan. Increasing the height of the vertical legs is desired in some clinical applications because the longer legs can be driven deeper into the tissue, thereby improving the tissue seal and/or hemostasis at the surgical site.

One of the features of conventional staple cartridges that limit its minimum size (and also limits the height of the staples) is the design of the staple pushers within the cartridges. Typically, the back span of the staple rides generally coincidental to the top surface of the staple pusher. To accommodate a taller staple, the pusher may be shortened, the cartridge made taller, or some combination of these two. However, the pusher can only be shortened so much before it becomes either too weak to withstand required loads, or susceptible to rocking during actuation. Likewise, constraints on overall instrument size may preclude making the staple cartridge taller or larger.

Accordingly, while the new telesurgical systems and devices have proven highly effective and advantageous, still further improvements would be desirable. In general, it would be desirable to provide improved surgical instruments that are more compact and maneuverable to enhance the efficiency and ease of use of minimally invasive systems. To that end, it would be beneficial to create staple pushers designed to accommodate taller staples to enhance the sealing performance of the surgical device and/or create smaller staple cartridges that will, in turn, allow for the design of more compact and maneuverable surgical instruments.

SUMMARY

The following presents a simplified summary of the claimed subject matter in order to provide a basic understanding of some aspects of the claimed subject matter. This summary is not an extensive overview of the claimed subject matter. It is intended to neither identify key or critical elements of the claimed subject matter nor delineate the scope of the claimed subject matter. Its sole purpose is to present some concepts of the claimed subject matter in a simplified form as a prelude to the more detailed description that is presented later.

The present disclosure provides a staple cartridge for a surgical instrument comprising a staple pusher and a staple. The staple pusher has a body with upper and lower surfaces and a recess in the upper surface. The staple has first and second legs and a backspan adjoining the first leg to the second leg. At least a portion of the backspan of the staple is configured to fit within the recess of the staple pusher. Preferably, the recess forms a pocket in the staple pusher body and the backspan of the staple resides entirely within the pocket and below the upper surface of the staple pusher. This provides additional vertical space for the staple such that a taller staple may be used in a staple cartridge of a given size, enhancing the sealing performance of the staple during use in surgery. Alternatively, a smaller staple cartridge may be designed for use with a staple having the same height, allowing for a more compact and maneuverable surgical instrument.

In one embodiment, the staple pusher body comprises a support element extending above the recess or pocket in the top surface of the body. The support element preferably comprises a substantially circumferential wall surrounding the pocket to provide additional support to the staple along the backspan and the bend radius between the legs and backspan. In an exemplary embodiment, the circumferential wall is an extension of the pusher body, extending above and almost completely around the pocket. This support minimizes undesirable transfer of forming loads to the backspan, allowing the staple to remain in place before use and minimizing potential malformation of the staple during use. In addition, the circumferential support element maintains adequate staple pusher height to assure stability against rocking, and structural robustness to the component.

Preferably, the distance between the top and bottom surfaces of the staple pusher (i.e., the maximum height of the staple pusher) is greater than the distance between the bottom surface of the staple pusher and the central surface of the pocket (i.e., minimum height of the pocket). Applicant has discovered that there is a critical ratio between these two distances that maximizes the height of the staple relative to the size of a given surgical instrument, while providing sufficient support for the staple and allowing for a sufficient volume of material in the staple pusher to withstand structural loads during use. The critical ratio of (i) the distance from the bottom of the staple pusher to the bottom surface of the pocket, to (ii) the total height of the staple pusher, is preferably less than about 0.6 to about 1.0. In one embodiment, this ratio is about 0.53 to about 1.0.

In certain embodiments, the transition between each of the first and second legs and the backspan is defined by a curve having a bend radius of at least 0.015 inches, more preferably between about 0.015 inches to 0.030 inches. The recess of the staple pusher preferably includes first and second curvilinear surfaces or ramps adjoined together by a central surface therebetween. The curved transition of the staple preferably extends along the ramps of the pusher such that they reside substantially in the pocket below the upper surface of the staple pusher body. This configuration allows the staple to be designed with a larger bend radius between the legs and backspan than conventional staples in surgical instruments. A transition having a larger bend radius facilitates staple formation in certain situations, at least by permitting additional wall support to be designed around the staple. This additional wall support effectively allows the staple pusher to be made taller without compromising pusher length.

In another aspect of the invention, a surgical instrument in accordance with this disclosure includes an end effector including first and second jaws configured to move relative to each other between open and closed positions. The surgical instrument further comprises a staple cartridge coupled to one of the first or second jaws. The staple cartridge includes a staple pusher having a body with upper and lower surfaces and a recess in the upper surface and a staple having first and second legs and a backspan adjoining the first leg to the second leg. The backspan of the staple is configured to fit within the recess of the staple pusher, preferably such that it resides entirely within the recess and below the upper surface of the staple pusher.

In certain embodiments, the surgical instrument further includes a drive member configured to translate distally and, in some embodiments, retract proximally through the end effector. The drive member has a central portion that translates through a channel in the fixed jaw. The central portion may be, for example, a cutting instrument, such as a knife, configured to cut tissue grasped between the first and second jaws when the jaws are in the closed position. The drive member further includes at least one outer portion spaced laterally from the central portion and having an inclined surface or ramp configured to engage the staple assemblies. The staple cartridge comprises an elongated housing with a rail extending substantially perpendicular to the longitudinal axis of the housing. The staple pusher comprises a body with a substantially circumferential surface having a groove sized and aligned to receive the rail of the staple cartridge. As the drive member is translated distally, the drive member ramp forces the staple pushers and staples in a perpendicular direction to the longitudinal axis of the housing to drive the staples into tissue.

In another aspect of the invention, the surgical instrument further includes an actuation mechanism in contact with the central portion of the drive member. The actuation mechanism is configured to advance the drive member distally through the end effector and to retract the drive member proximally through the end effector. In an exemplary embodiment, the actuator includes a control device of a robotic telesurgical system that may, for example, allow for mechanical actuation and control of the surgical instrument to perform a variety of functions, such as grasping a blood vessel, dissecting tissue, or the like, in response to manipulation of master input devices located remotely from the surgical instrument.

In yet another embodiment of the invention, a staple support for a surgical instrument comprises a body with upper and lower surfaces and a recess in the upper surface that forms a pocket for receiving at least a portion of a staple. The staple support further includes a support element surrounding at least a portion of the pocket to provide additional support to the staple. The support element preferably comprises a substantially circumferential wall surrounding the pocket. In an exemplary embodiment, the circumferential wall is integral with the staple pusher body. The pocket in the staple support body preferably includes first and second curved surfaces or ramps adjoined together by a central surface therebetween. The curved surfaces preferably have a bend radius suitable to provide support for the curved.

It is to be understood that both the foregoing general description and the following detailed description are exemplary and explanatory only and are not restrictive of the disclosure. Additional features of the disclosure will be set forth in part in the description which follows or may be learned by practice of the disclosure.

BRIEF DESCRIPTION OF THE DRAWINGS

The accompanying drawings, which are incorporated in and constitute a part of this specification, illustrate several embodiments of the disclosure and together with the description serve to explain the principles of the disclosure.

DETAILED DESCRIPTION

This description and the accompanying drawings illustrate exemplary embodiments and should not be taken as limiting, with the claims defining the scope of the present disclosure, including equivalents. Various mechanical, compositional, structural, and operational changes may be made without departing from the scope of this description and the claims, including equivalents. In some instances, well-known structures and techniques have not been shown or described in detail so as not to obscure the disclosure. Like numbers in two or more figures represent the same or similar elements. Furthermore, elements and their associated aspects that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment. Moreover, the depictions herein are for illustrative purposes only and do not necessarily reflect the actual shape, size, or dimensions of the system or illustrated components.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

While the following disclosure is presented with respect to a linear surgical stapler where staples are sequentially fired, it should be understood that the features of the presently described surgical instruments may be readily adapted for use in any type of surgical clamping, cutting, or sealing instruments, whether or not the surgical clamping and cutting instrument applies a fastener. For example, the presently described drive member and actuation mechanism may be employed in an electrosurgical instrument wherein the jaws include electrodes for applying energy to tissue to treat (e.g., cauterize, ablate, fuse, or cut) the tissue. The surgical clamping and cutting instrument may be a minimally invasive (e.g., laparoscopic) instrument or an instrument used for open surgery.

Additionally, the features of the presently described surgical stapling instruments may be readily adapted for use in surgical instruments that are activated using any technique within the purview of those skilled in the art, such as, for example, manually activated surgical instruments, powered surgical instruments (e.g., electro-mechanically powered instruments), robotic surgical instruments, and the like.

Figure 1:
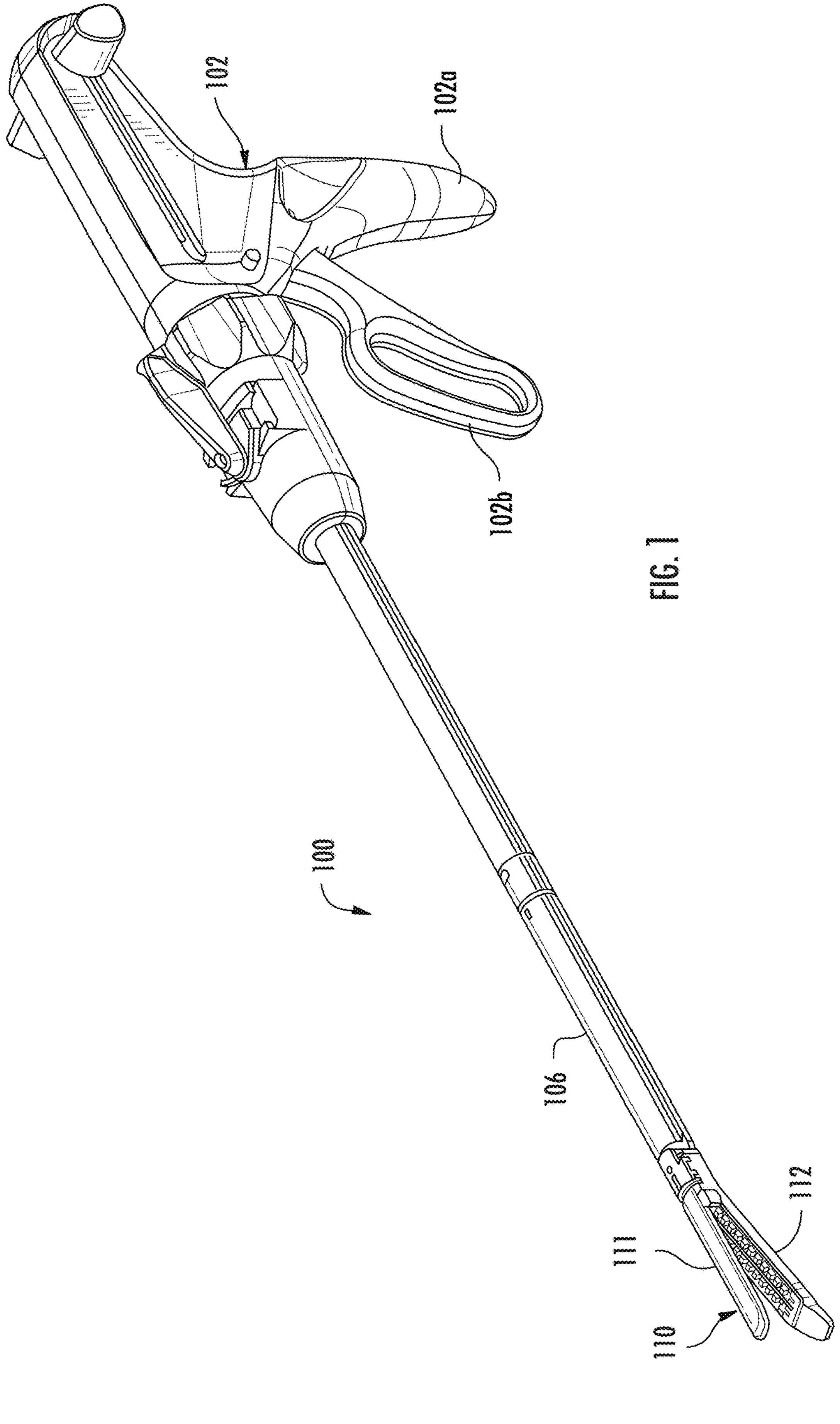
FIG. 1 illustrates a perspective view of an illustrative surgical instrument having an end effector mounted to an elongated shaft.

FIG. 1 is a perspective view of an illustrative surgical instrument 100 in accordance with certain embodiments of the present disclosure having a handle assembly 102, and an end effector 110 mounted on an elongated shaft 106 of the surgical stapling instrument 100. End effector 110 includes a first jaw 111 and a second jaw 112. Handle assembly 102 includes a stationary handle **102*a* and a moveable handle 102*a*, which serves as an actuator for surgical instrument 100**.

In certain embodiments, handle assembly 102 may include input couplers (not shown) instead of, or in addition to, the stationary and movable handles. The input couplers provide a mechanical coupling between the drive tendons or cables of the instrument and motorized axes of the mechanical interface of a drive system. The input couplers may interface with, and be driven by, corresponding output couplers (not shown) of a telesurgical surgery system, such as the system disclosed in U.S. Pub. No. 2014/0183244A1, the entire disclosure of which is incorporated by reference herein. The input couplers are drivingly coupled with one or more input members (not shown) that are disposed within the instrument shaft 106 and end effector 110. Suitable input couplers can be adapted to mate with various types of motor packs (not shown), such as the stapler-specific motor packs disclosed in U.S. Pat. No. 8,912,746, or the universal motor packs disclosed in U.S. Pat. No. 8,529,582, the disclosures of both of which are incorporated by reference herein in their entirety. Further details of known input couplers and surgical systems are described, for example, in U.S. Pat. Nos. 8,597,280, 7,048,745, and 10,016,244. Each of these patents is hereby incorporated by reference in its entirety.

Actuation mechanisms of surgical instrument 100 may employ drive cables that are used in conjunction with a system of motors and pulleys. Powered surgical systems, including robotic surgical systems that utilize drive cables connected to a system of motors and pulleys for various functions including opening and closing of jaws, as well as for movement and actuation of end effectors are well known. Further details of known drive cable surgical systems are described, for example, in U.S. Pat. Nos. 7,666,191 and 9,050,119 both of which are hereby incorporated by reference in their entireties. While described herein with respect to an instrument configured for use with a robotic surgical system, it should be understood that the wrist assemblies described herein may be incorporated into manually actuated instruments, electro-mechanical powered instruments, or instruments actuated in any other way.

Figure 1A:
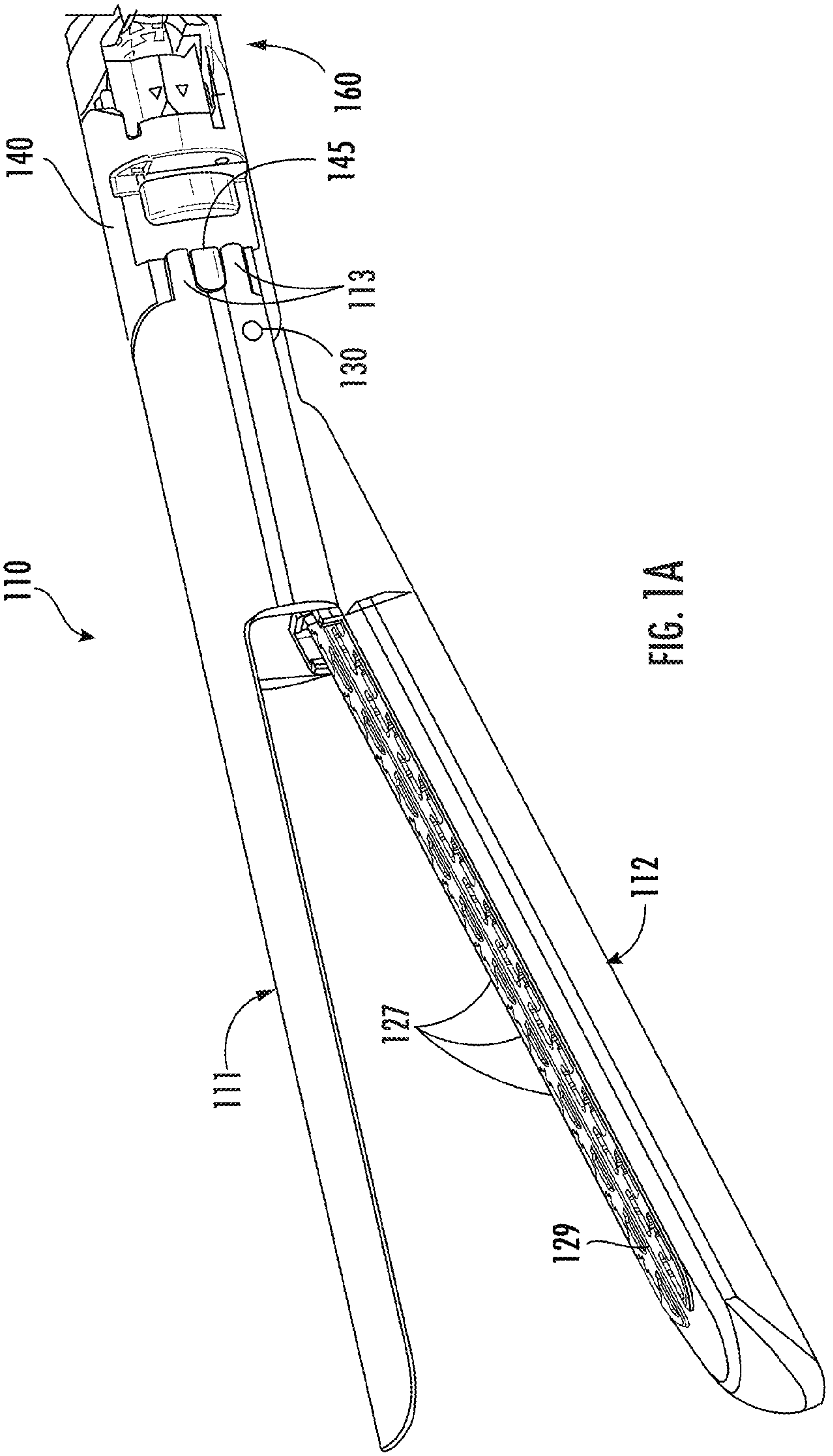
FIG. 1A is a perspective top view of the distal end portion of an illustrative surgical instrument with the jaws in the open position.

FIG. 1A illustrates the distal end portion of surgical instrument 100, including an end effector 110 having first and second jaws 111, 112, a clevis 140 for mounting jaws 111, 112 to the instrument, and an articulation mechanism, such as a wrist 160. First jaw 111 includes an anvil 115 having staple-forming pockets 116 (see FIG. 1D). In certain embodiments, second jaw 112 is a movable jaw configured to move from an open position to a closed position relative to first jaw 111. In other embodiments, first jaw 111 is a movable jaw configured to move between open and closed positions relative to second jaw 112. In still other embodiments, both jaws 111, 112 are movable relative to each other. In the open position, a fresh stapling cartridge 122 (sometimes referred to as a reload and shown more clearly in FIG. 1B) can be loaded into movable jaw 112 and tissue may be positioned between the jaws 111, 112. In the closed position, jaws 111, 112 cooperate to clamp tissue such that cartridge 122 and the anvil 115 are in close cooperative alignment.

Figure 1B:
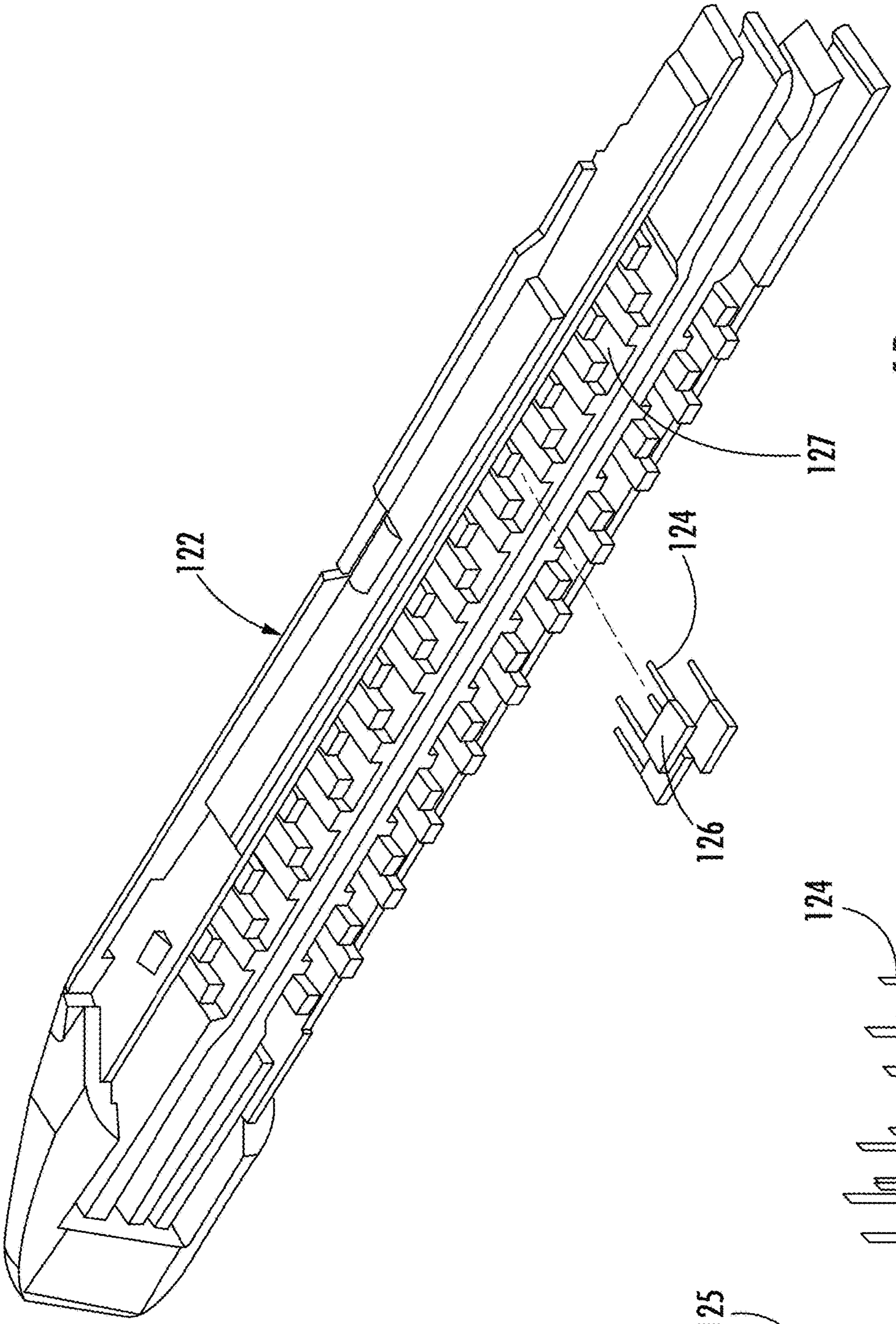
FIG. 1B is a bottom perspective view with parts separated of a representative staple cartridge for an illustrative surgical instrument.
Figure 1C:
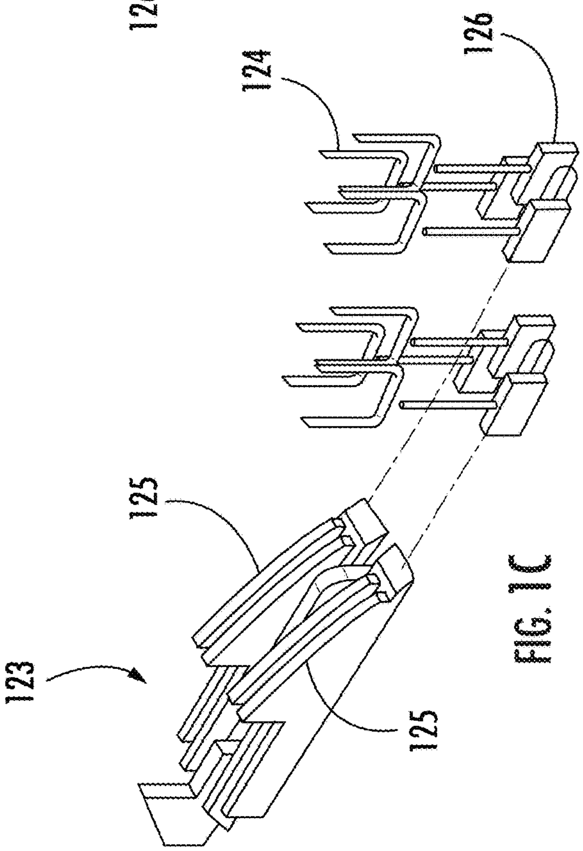
FIG. 1C shows an enlarged view of the cooperative relationship between a portion of a drive member and a plurality of staple pushers and staples which form part of the staple cartridge of FIG. 1B.
Figure 1D:
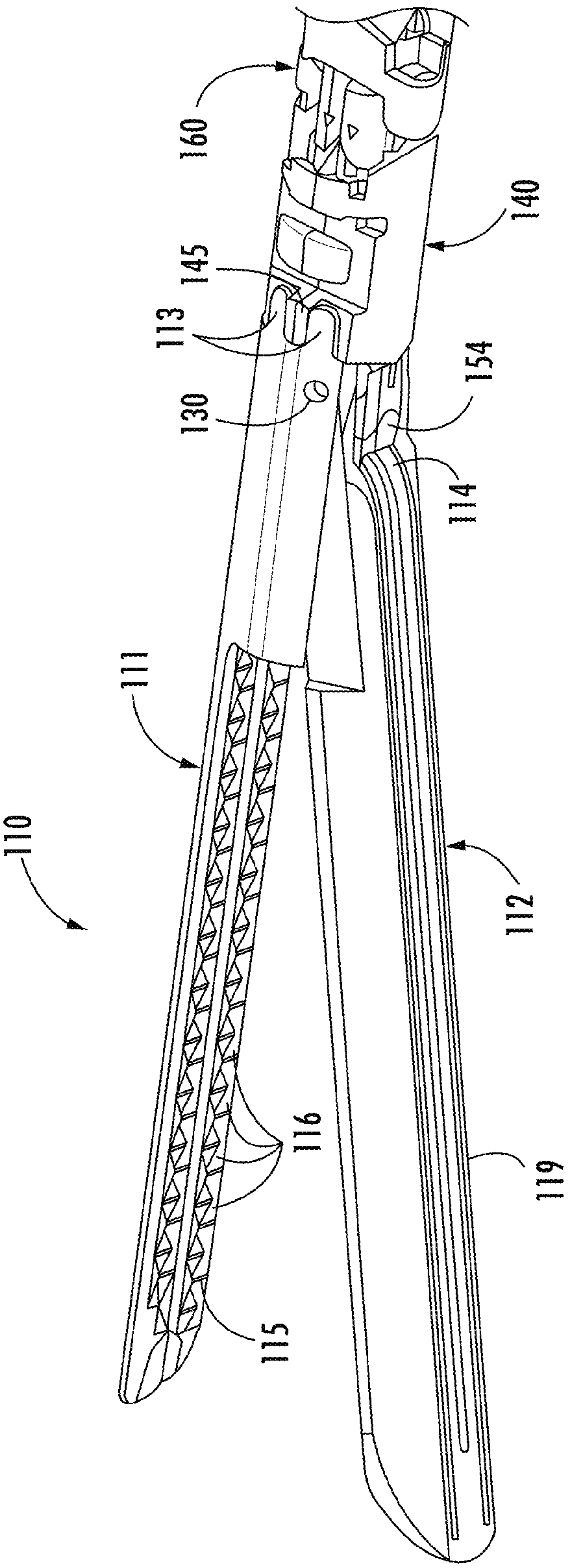
FIG. 1D is a perspective bottom view of the distal end portion of the surgical instrument of FIG. 1A.

Referring now to FIGS. 1B and 1C, a representative staple cartridge 122 may include a plurality of staples assemblies, each comprising one or more staples 124 supported on corresponding staple drivers or pushers 126 provided within respective staple apertures 127 formed in cartridge 122. In certain embodiments, cartridge 122 also may include a shuttle 123 having an inclined distal surface 125 that, upon distal movement, sequentially acts on staple pushers 126, camming them upwardly, thereby moving staples 124 into deforming contact with anvil 115 (See FIG. 1D). Shuttle 123 may be part of a drive member 150 (FIGS. 6A and 6B) described in more detail below. Cartridge 122 may be removably received within movable jaw 112 or, in single use embodiments, may be manufactured as part of movable jaw 112.

Figure 4:
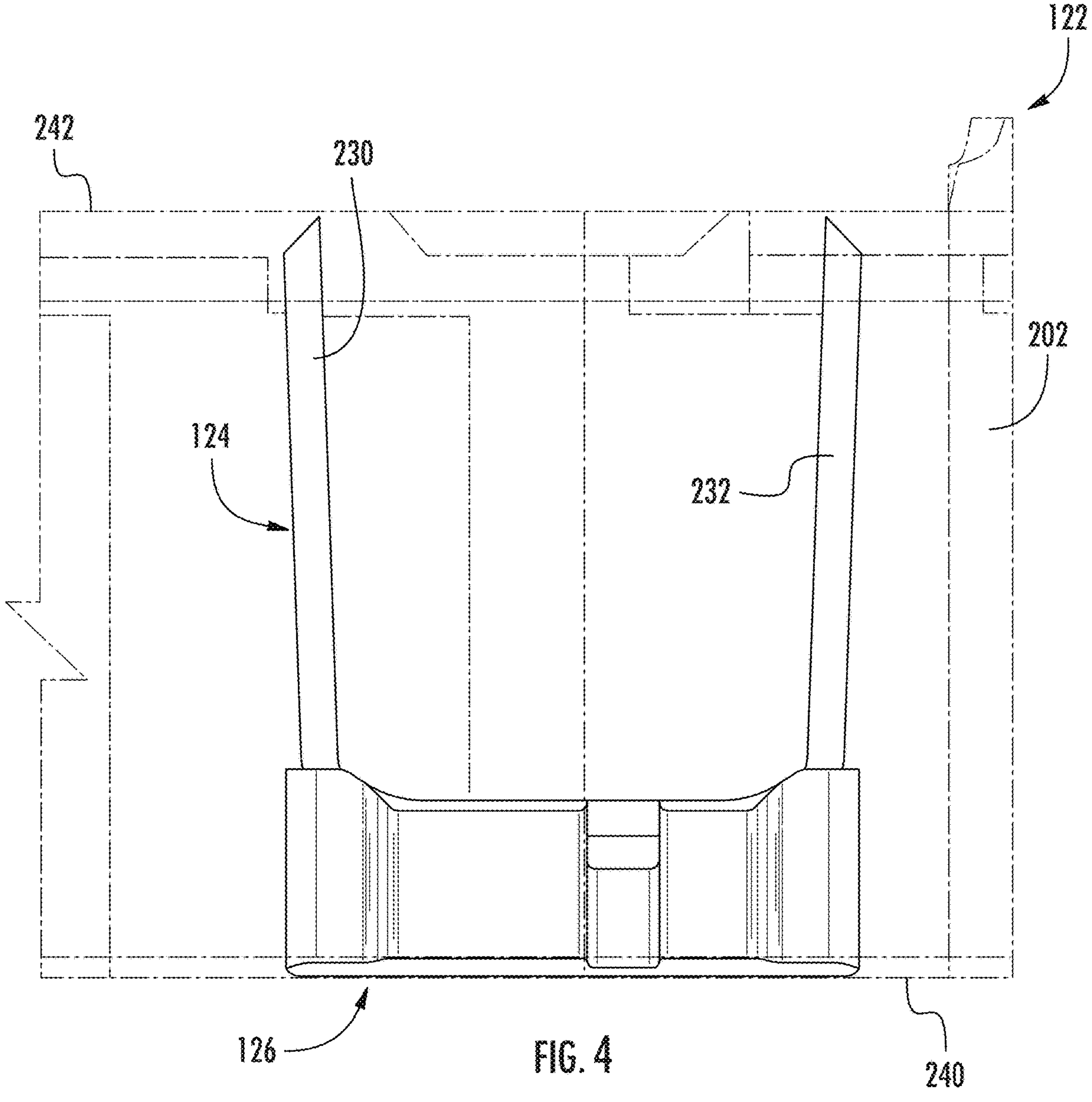
FIG. 4 is a semi-transparent view of portion of a staple cartridge with a staple pusher and staple according to an embodiment of the present disclosure.

Referring now to FIGS. 1B and 4, a preferred embodiment of cartridge 122 will now be described. As shown, cartridge 122 includes a housing extending substantially along a longitudinal axis and including a plurality of compartments that form pockets within the housing to receive the staple assemblies. The staple assemblies each include at least one (preferably 2-4) staple pushers 126 removably coupled to at least one (preferably 2-4) staples 124. The staple assemblies are preferably arranged within the compartments such that staple pusher 126 is situated near a bottom surface 240 of housing 202 and staples 124 have their legs facing a top surface 242 of housing 202. For ease of reference, the top surface of housing faces fixed jaw 111 (see FIG. 1). As discussed above, the entire staple cartridge 122 can be loaded into movable jaw 112 for use in surgery as described in more detail below.

Figure 2:
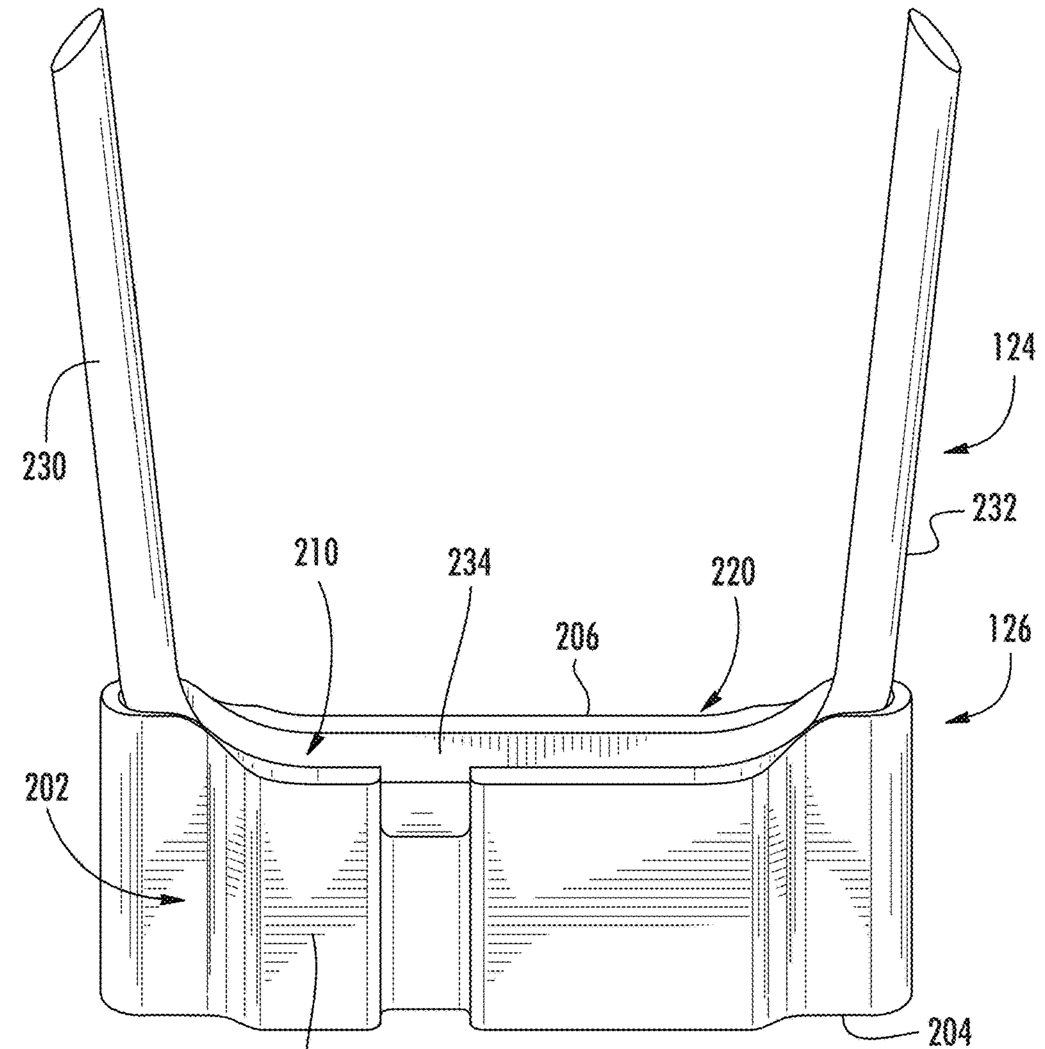
FIG. 2 is a perspective view of a staple pusher and a staple according to one embodiment of the present invention.
Figure 3:
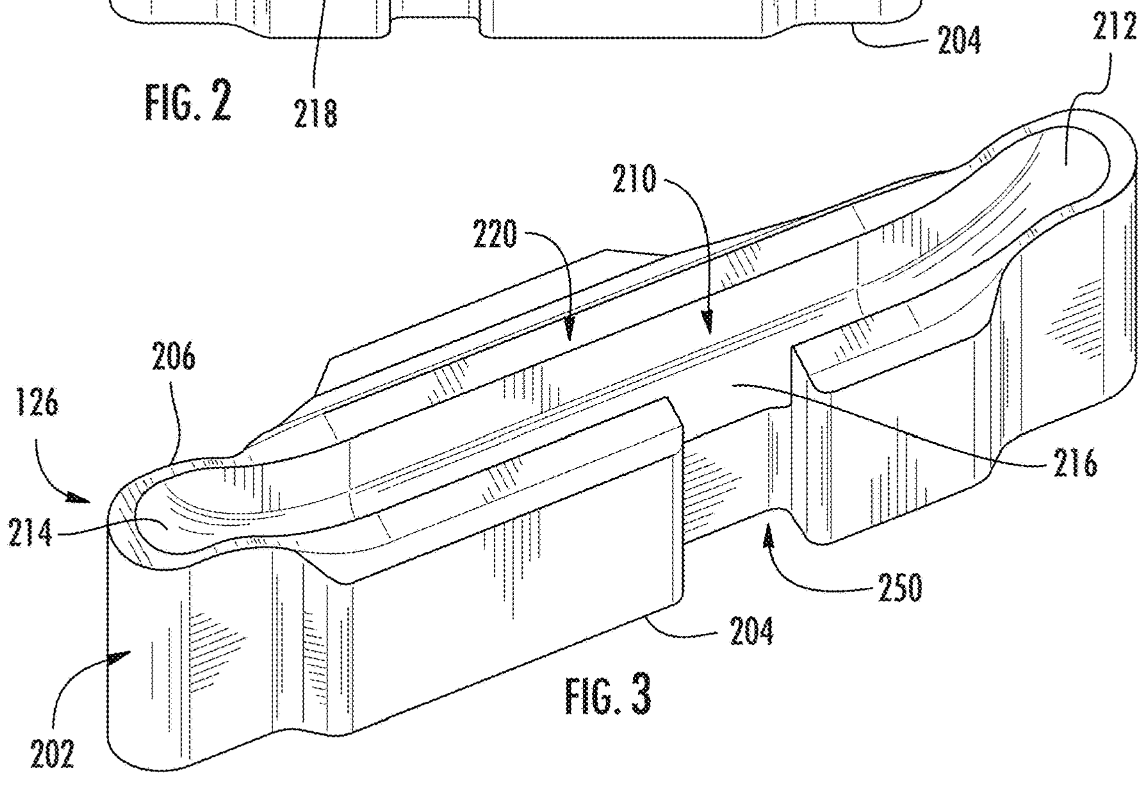
FIG. 3 is a perspective top view of the staple pusher of FIG. 2.

Referring now to FIGS. 2-4, a preferred embodiment of staple 124 and staple pusher 126 according to the present disclosure will now be described. Staple pusher 126 comprises an elongated body 202 with a substantially planar bottom surface 204 and a top surface 206. Body 202 preferably comprises a substantially unitary member with a geometry primarily designed to provide support to staple 124, fit within cartridge 122 so as to perform its function and to withstand the loads applied to pusher 126 during deployment. Thus, body 202 will preferably have a length and width that is only slightly larger than the corresponding length and width of the backspan of the surgical staple being used for the clinical application. However, it will be recognized by those skilled in the art that body 202 is not limited to the precise geometrical shape shown in FIGS. 2 and 3. In addition, body 202 may be formed from two or more parts that are suitably coupled together.

A recess in top surface 206 forms a pocket 210 in body 202 for receiving staple 124. Pocket 210 preferably includes first and second outer curved surfaces or ramps 212, 214 adjoined together with a central (substantially planar) surface 216. Curved surfaces 212, 214 allow for a larger bend radii for the staple legs and more support for staple 124 within pocket 210, as discussed in more detail below. Pocket 210 may, however, have other suitable dimensions and/or geometries to accommodate different staples and/or to accommodate different clinical applications. For example, although applicant has found the above radius of curvature to be advantageous, the angles of surfaces 212, 214 relative to the flat portion of surface 216 may be anywhere between about 90 degrees to about 135 degrees, depending on the size and shape of staple 124 and/or the desired clinical application.

In the exemplary embodiment, top surface 206 of staple pusher 126 generally ramps upwards on the two ends of pusher 126 such that it substantially conforms to the geometry of surface 216 and curved surfaces 212, 214 of pocket 210. Applicant has found that this configuration provides sufficient support to allow pusher 126 to perform its functions. The present invention, however, is not limited to this configuration and top surface 206 may comprise other configurations or geometries so long as it forms a suitable pocket 210 for staple 124 according to the present invention. For example, top surface 206 may be substantially planar such that the central section of top surface 206 is higher than shown in the figures (i.e., a shallower pocket having less or no ramping upward on the ends of top surface 206 to conform to the geometry of pocket 210).

Staple 124 comprises first and second legs 230, 232 and a backspan 234 therebetween. Legs 230, 232 are typically formed slightly open to allow their tips to bear on the ends of cartridge 122 and retain staple 124 within cartridge 122 prior to deployment. In the present invention, the bend radii between each of legs 230, 232 and backspan 234 is preferably at least about 0.015 inches, more preferably between about 0.015 inches to about 0.030 inches. The configuration of pocket 210 allows the bend radius of staple 126 to be greater than conventional staples in surgical instruments. A larger bend radius in the present invention can in certain instances minimize malformation of staple 126 during use. In addition, increasing the bend radius of staple 124 allows for additional wall support around the staple, effectively allowing pusher 126 to be made taller without compromising its longitudinal length (i.e., the length of backspan 234). This is important because the longitudinal spacing of staples 124 within cartridge 122 is preferably designed such that staples 124 are very close to each other to assure appropriate hemostasis at the surgical site. As a result, the longitudinal length of pusher 126 is preferably not significantly longer than backspan 234 of staple 124. Otherwise, staples 124 would be spaced further apart from each other within cartridge 122, potentially compromising the sealing efficiency of the surgical device.

Staple pusher 126 includes an outer surface 218 substantially surrounding body 202 (except for groove 250 discussed below) between top and bottom surfaces 204, 206. As shown, outer surface 218 extends above pocket 210 to form a substantially circumferential wall 220 surrounding pocket 210 to provide support for staple 124 (see FIG. 2). Pocket 210 is preferably deep enough such that the entire backspan 234 of staple 126 fits within pocket 210. In addition, the bend radii between each of legs 230, 232 and backspan 234 of staple 124 also preferably fit within pocket 210 along curved surfaces 212, 214. This additional support ensures that staple 124 will remain in contact with pusher 126 prior to use. In addition, it provides support for staple 124 during use to minimize malformation of legs 230, 232.

Circumferential wall 220 may have other configurations. For example, wall 220 may be configured to only surround a portion of backspan 210 (i.e., a central wall on either side of pocket 210 without any material at the two ends of pusher body 202) or wall 220 may only be formed at the ends of pusher 126 without any material in the center. Alternatively, wall 220 may have gaps at certain points along its circumference, or it may not be an actual wall that surrounds pocket, but a series of support posts that extend upwards from pusher body 204 above pocket 210 at suitable locations to provide support for staple 124.

Applicant has discovered that there are certain critical dimensions for staple pusher 126 that provide sufficient support and material strength to perform its function, while maximizing the height of staple 124 within a cartridge 122 of a given size. The exact dimensions will vary depending on the size and functionality of cartridge 122. However, applicant has found that certain ratios of dimensions will maximize performance. To that end, the maximum height of pusher 126 can be defined as the distance from lower surface 204 to top surface 206 at the ends of pusher 126 (i.e., where top surface 206 extends the furthest distance from bottom surface 204). The minimum height of pocket 210 can be defined as the distance from lower surface 204 of body 202 to central surface 216 of pocket 210. Applicant has discovered that there is a critical ratio between these two distances that maximizes the height of the staple relative to the size of a given surgical instrument, while providing sufficient support for the staple and allowing for a sufficient volume of material in the staple pusher to withstand structural loads during use. The critical ratio of (i) the distance from the bottom of the staple pusher 204 to bottom surface 216 of the pocket, to (ii) the total height of the staple pusher, is preferably less than about 0.6 to 1. Thus, the distance from the lower surface of the staple pusher to an inner surface of the recess is less than 60% of a distance between the upper and lower surfaces of the staple pusher. In one embodiment, Thus, this ratio is about 0.53 to 1, i.e., the distance from the lower surface of the staple pusher to an inner surface of the recess is about 53% of a distance between the upper and lower surfaces of the staple pusher.

As shown in FIG. 3, staple pusher 126 further comprises a groove 250 within outer surface 218 for receiving a substantially linear projection, rib or rail (not shown) in cartridge 122. Groove 250 extends from bottom surface 204 to top surface 206 and is sized to engage with the cartridge rail and allow for movement of staple pusher 126 in a substantially perpendicular direction to the longitudinal axis of cartridge housing 202. Groove 250 ensures that when drive member 150 is translated distally, staple pusher 126 and staple 124 do not move distally and are instead driven upwards along the cartridge rail so that staple 124 is ultimately driven into the tissue when movable jaw 112 engages fixed jaw 110.

In other embodiments, pusher 124 may be formed without groove 250. In these embodiments, other mechanisms can be used to ensure that staple pusher 124 is driven upwards into fixed jaw 110 during actuation. For example, cartridge 122 may include rails or other material at the distal end of each pusher 126 or at each staple assembly to prevent distal movement of staple assemblies when drive member 150 engages them. In this configuration, pusher 124 will not have a groove and the circumferential wall 220 may extend completely around pocket 210.

FIG. 4 illustrates a semi-transparent view of one portion of staple cartridge 122. As shown, bottom surface 204 of staple pusher 126 preferably resides near bottom surface 240 of staple cartridge 122. Pusher 126 and staple 124 are configured such that the tips of staple legs 230, 232 preferably reside substantially near top surface 242 of staple cartridge 122.

In the present invention, pocket 210 of staple pusher 126 provides additional vertical space for staple 124. Therefore, staple cartridge 122 may be designed with taller staples than conventional staples and/or the overall cartridge may have a smaller overall profile (e.g., diameter) than conventional staple cartridges. In an exemplary embodiment, staple cartridge 122 of the present invention preferably has a diameter less than 12 mm, more preferably about 8 mm. This smaller diameter cartridge allows for the design of a smaller and more compact surgical instrument, which provides the surgeon with more maneuverability during a surgical procedure. In addition, the smaller and more compact surgical instrument is less likely to contact and possibly damage collateral tissue in the surgical arena.

In certain embodiments, jaws 111, 112 are attached to surgical instrument 100 via a suitable coupling device, such as a clevis 140. Clevis 140 includes upper and lower portions that cooperate when assembled to form a protrusion 145 configured to engage tabs 113 (see FIG. 1A) of jaw 111 to securely mount jaw 111 in a fixed position on instrument 100. Clevis 140 further includes an opening for receiving a pivot pin 130 defining a pivot axis around which jaw 112 pivots as described in more detail below. A more complete description of a suitable clevis 140 for use with the present invention may be found in commonly-assigned, provisional patent application No. 62/783,444, filed Dec. 21, 2018; 62/783,481, filed Dec. 21, 2018; 62/783,460, filed Dec. 21, 2018; 62/747,912, filed Oct. 19, 2018; and 62/783,429, filed Dec. 21, 2018, the complete disclosures of which are hereby incorporated by reference in their entirety for all purposes. Of course, it will be recognized by those skilled in the art that other coupling mechanisms known by those skilled in the art may be used with the present invention to attach the jaws 111, 112 to the proximal portion of surgical instrument 100.

Figure 5:
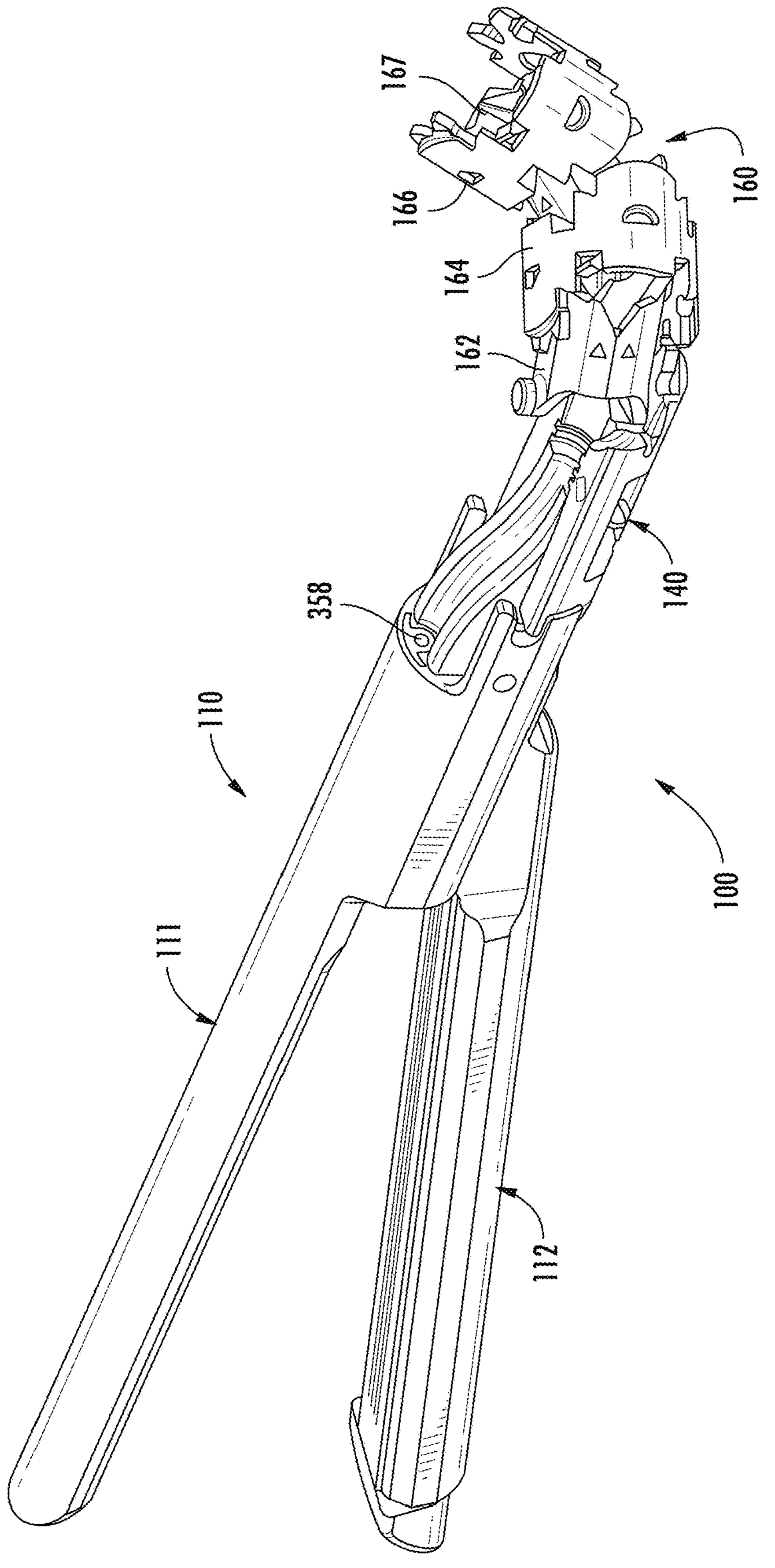
FIG. 5 is a perspective view of the end portion of an illustrative surgical instrument with parts removed.

Referring now to FIG. 5, end effector 110 may be articulated in multiple directions by an articulation mechanism. In certain embodiments, the articulation mechanism may be a wrist 160 as shown, although other articulation mechanisms are contemplated. As shown, a preferred embodiment of wrist 160 includes a plurality of articulation joints 162, 164, 166, etc. that define a bore 167 through which an actuation mechanism (in certain embodiments, coil 120 and drive cable 171, see FIG. 6A) may pass. Upon exiting articulation wrist 160, coil 120 enters and passes through an internal channel (not shown) of clevis 140, ultimately engaging a proximal surface of upper shoe 152 of drive member 150 (see FIG. 7A). Other articulation mechanisms known by those skilled in the art may substitute for wrist 160. Other exemplary articulating mechanisms are shown for example in commonly-assigned, co-pending U.S. Publication No. 2015/0250530 and International Application No. PCT/US19/62344, filed Nov. 20, 2019, the entire disclosures of which are hereby incorporated by reference in their entirety for all purposes.

Figure 6B:
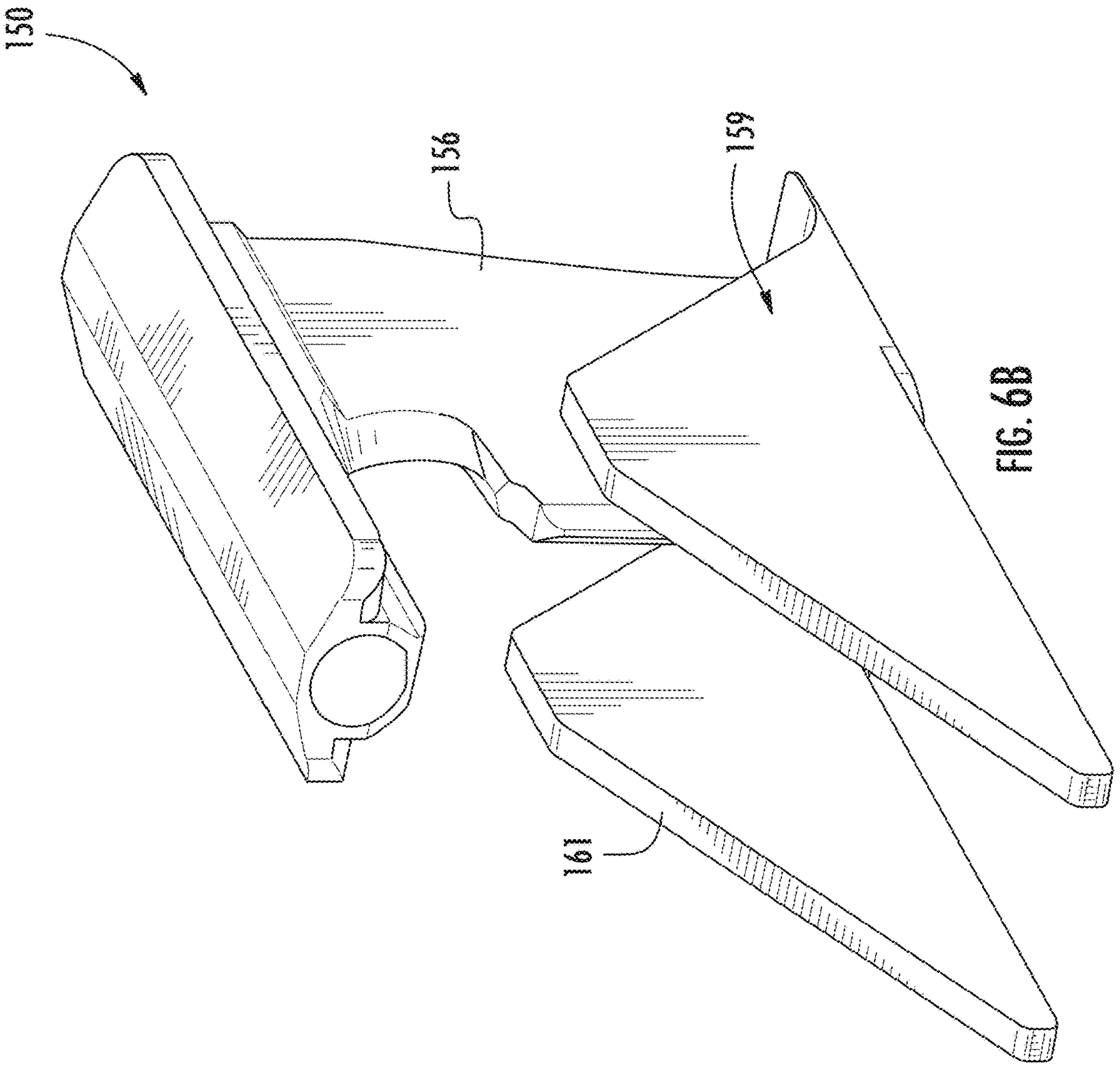
FIG. 6B is a side view of the drive member of FIG. 6A.
Figure 6A:
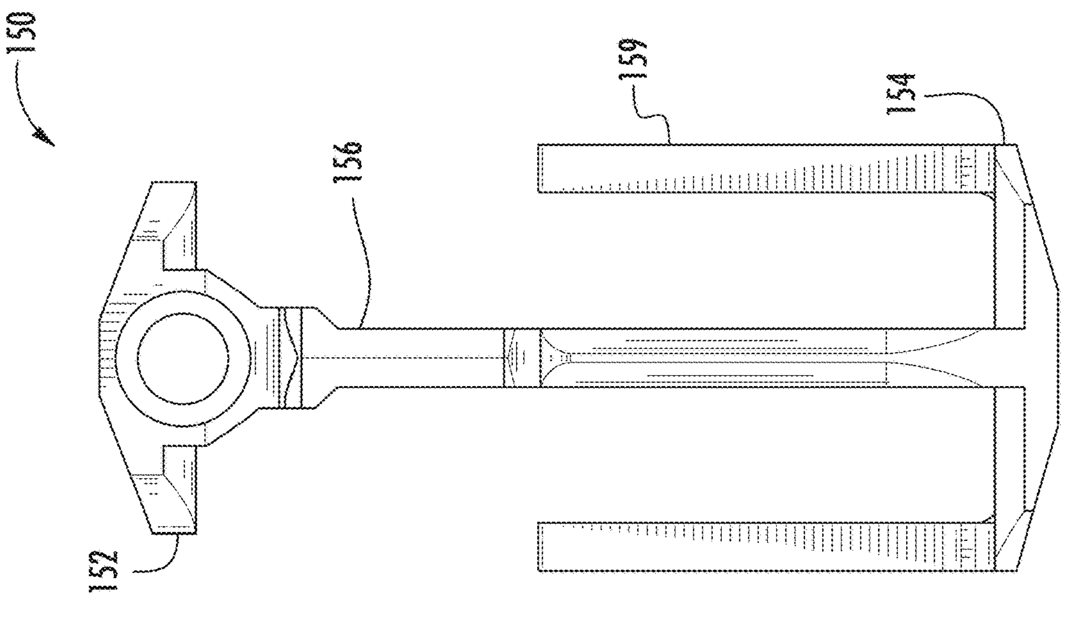
FIG. 6A is a front view of a drive member for the illustrative surgical instrument of FIG. 1.

As seen in FIGS. 6A and 6B, a preferred embodiment of drive member 150 may include a body having an upper projection or shoe 152, a lower projection or shoe 154, a central portion 156 and first and second lateral portions 159. Lateral portions 159 are the fins that form shuttle 123 shown earlier. Lateral portions 159 of drive member 150 each comprise distal inclined surfaces or ramps 161 that engage with pushers 126 to drive pushers 126 (and the associated staples 124) vertically or perpendicular to the longitudinal axis of shaft 106 when drive member 150 is translated distally. In a preferred embodiment, shuttle fins 159 are integrated into lower shoe 154 of drive member 150. Integrating shuttle fins 159 into drive member 150 provides more flexibility in the design of staple cartridge 122. For example, this may allow for a reduction in the size of staple cartridge 122 and surgical instrument 100 and/or increasing the length of staples 124 for a given size of surgical instrument 100.

Figure 7A:
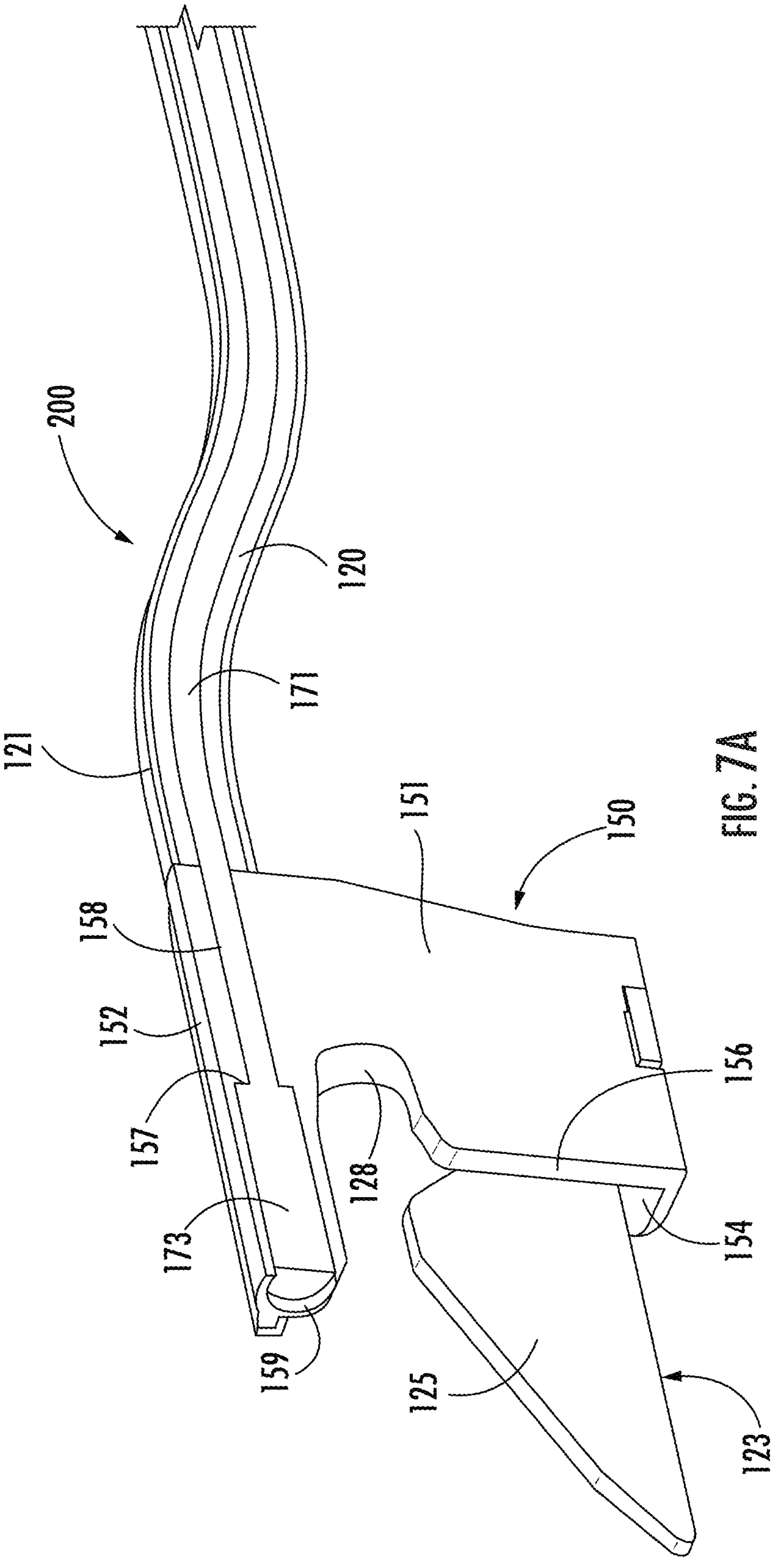
FIG. 7A is a partial cross-sectional perspective view of the actuation mechanism for a drive member in accordance with the surgical instrument of FIG. 1.
Figure 7B:
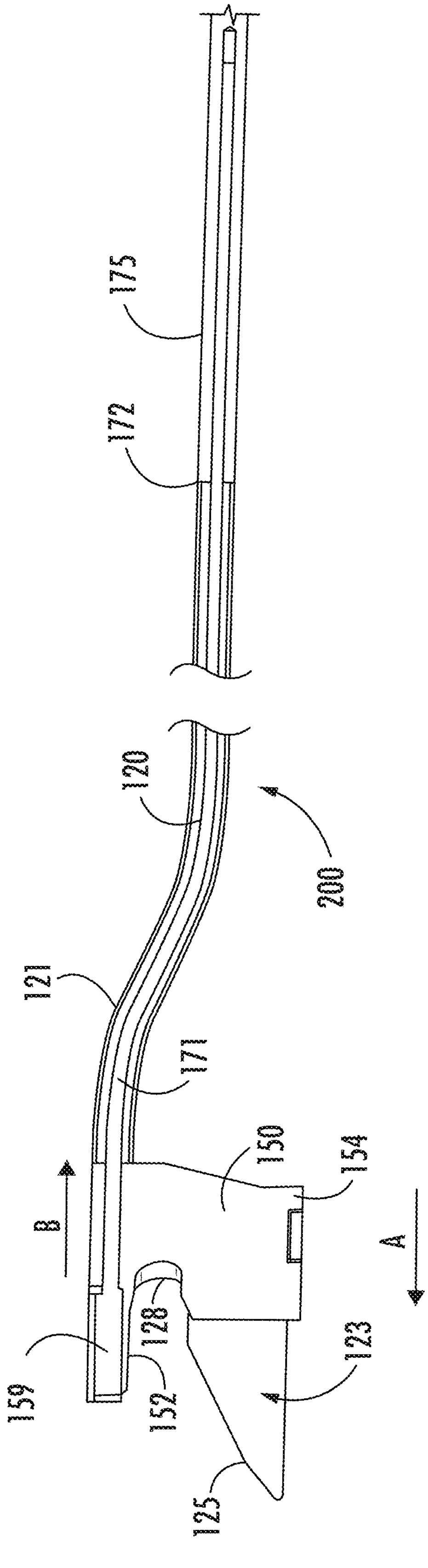
FIG. 7B is a partial cross-sectional side view of the actuation mechanism for a drive member in accordance with the surgical instrument of FIG. 1.

As shown in FIGS. 7A and 7B, actuation assembly 190 includes a drive cable 171, a coil 120, a sheath 121 surrounding coil 120, and a drive rod 175. Drive cable 171 includes an enlarged distal end 173. Upper shoe 152 of drive member 150 includes a bore 158 into which drive cables 171 are routed. When assembling illustrative surgical instrument 100, coil 120 and protective sheath 121 are slipped over the free end of drive cable 171. The free end of drive cable 171 is attached to drive rod 175 securing coil 120 and the protective sheath 121 between drive member 150 and drive rod 175 (as best seen in FIG. 7B). Sheath 121 may function to promote stability, smooth movement, and prevent buckling upon actuation of surgical instrument 100. Sheath 121 may be made from polyimide, or any other suitable material having the requisite strength requirements such as various reinforced plastics, a nickel titanium alloy such as NITI-NOL™, poly para-phenyleneterphtalamide materials such as KEVLAR™ commercially available from DuPont. Those of skill in the art may envision other suitable materials.

Enlarged distal end 173 of drive cable 171 resides within an enlarged distal portion 159 of bore 158 in upper shoe 152 of drive member 150, such that a proximal face 157 of enlarged distal end 173 may apply a retraction force on upper shoe 152 when the drive cable 171 is pulled proximally, i.e., in the direction of arrow "B" in FIG. 7B. Drive rod 175 is operationally connected to an actuator (e.g., movable handle 102*a*), which allows distal translation and proximal retraction of actuation assembly 190. Those skilled in the art will recognize that in a manually actuated instrument, the actuator may be a movable handle, such as moveable handle 102*a* shown in FIG. 1; in a powered instrument the actuator may be a button (not shown) that causes a motor to act on the drive rod; and in a robotic system, the actuator may be a control device such as the control devices described below in connection with FIGS. 9 and 10. Any suitable backend actuation mechanism for driving the components of the surgical stapling instrument may be used. For additional details relating to exemplary actuation mechanisms using push/pull drive cables see, e.g., commonly assigned, co-pending International Application No. WO 2018/049217, the disclosure of which is hereby incorporated by reference in its entirety.

Figure 8:
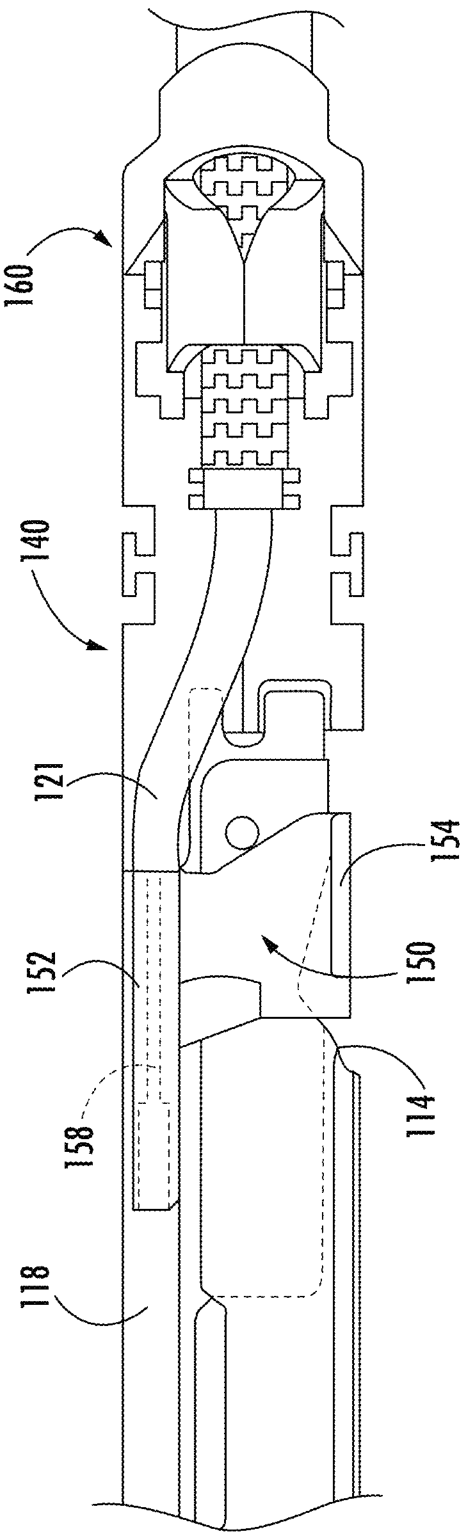
FIG. 8 is a cross-sectional side view of the end portion of the illustrative surgical instrument of FIG. 1.

Referring now to FIG. 8, upper shoe 152 of drive member 150 is substantially aligned with and translates through a channel 118 in fixed jaw 111, while lower shoe 154 of drive member 150 is substantially aligned with and translates through a channel (not shown) and below jaw 112. As shown in FIGS. 7A and 7B, bore 158 is formed through upper shoe 152 to receive drive cable 171 as will be described in more detail below. Proximal surface 153 of upper shoe 152 is configured to be engaged by a coil 120 of actuation assembly 190 such that coil 120 may apply force to upper shoe 152 to advance drive member 150 distally, i.e., in the direction of arrow "A" in FIG. 7B. A knife 128 may be formed on drive member 150 along the distal edge between upper shoe 152 and central portion 156.

During actuation of illustrative surgical instrument 100, drive rod 175 applies force to coil 120, thereby causing coil 120 to apply force to upper shoe 152 of drive member 150, translating it distally (i.e., in the direction of arrow "A" in FIG. 7B) initially closing jaws 111,112 and then ejecting staples 124 from cartridge 122 to staple tissue. After stapling is complete, drive rod 175 applies a force in the proximal direction to effect retraction of drive member. During retraction, enlarged distal end 173 of drive cable 171 is obstructed by wall 157 of enlarged portion 159 of bore 158, causing drive cable 171 to apply force to upper shoe 152 of drive member 150, thereby translating drive member 150 in the proximal direction. In certain embodiments, the surgical instrument may be designed such that the drive member 150 is not retracted in the proximal direction after the staples have been fired. One of ordinary skill in the art will appreciate that drive member 150, drive cable 171, and drive rod 175 all move in unison and remain in the same relative position to each other.

In use, in the open configuration, drive member 150 is positioned proximally of cam surface 114 formed on movable jaw 112. As drive member 150 translates in the distal direction, movable jaw 112 will rotate towards the closed position around pivot 117. Once drive member 150 has come into contact with cam surface 114 of movable jaw 112, lower portion 154 of drive member 150 rides underneath cam surface 114, drive member 150 pushes movable jaw 112, causing it to pivot towards the closed position. In the closed position, drive member 150 has translated distally past cam surface 114. In this position, tissue is clamped, and further advancement of the drive member will sever and staple tissue. Of course, it will be recognized by those skilled in the art that drive member 150 may be any structure capable of pushing at least one of a shuttle or a knife of a surgical stapling instrument with the necessary force to effectively sever or staple human tissue. Drive member 150 may be an I-beam, an E-beam, or any other type of drive member capable of performing similar functions. Drive member 150 is movably supported on the surgical stapling instrument 100 such that it may pass distally through a staple cartridge and upper fixed jaw 111 and lower jaw 112 when the surgical stapling instrument is fired (e.g., actuated).

Figure 9:
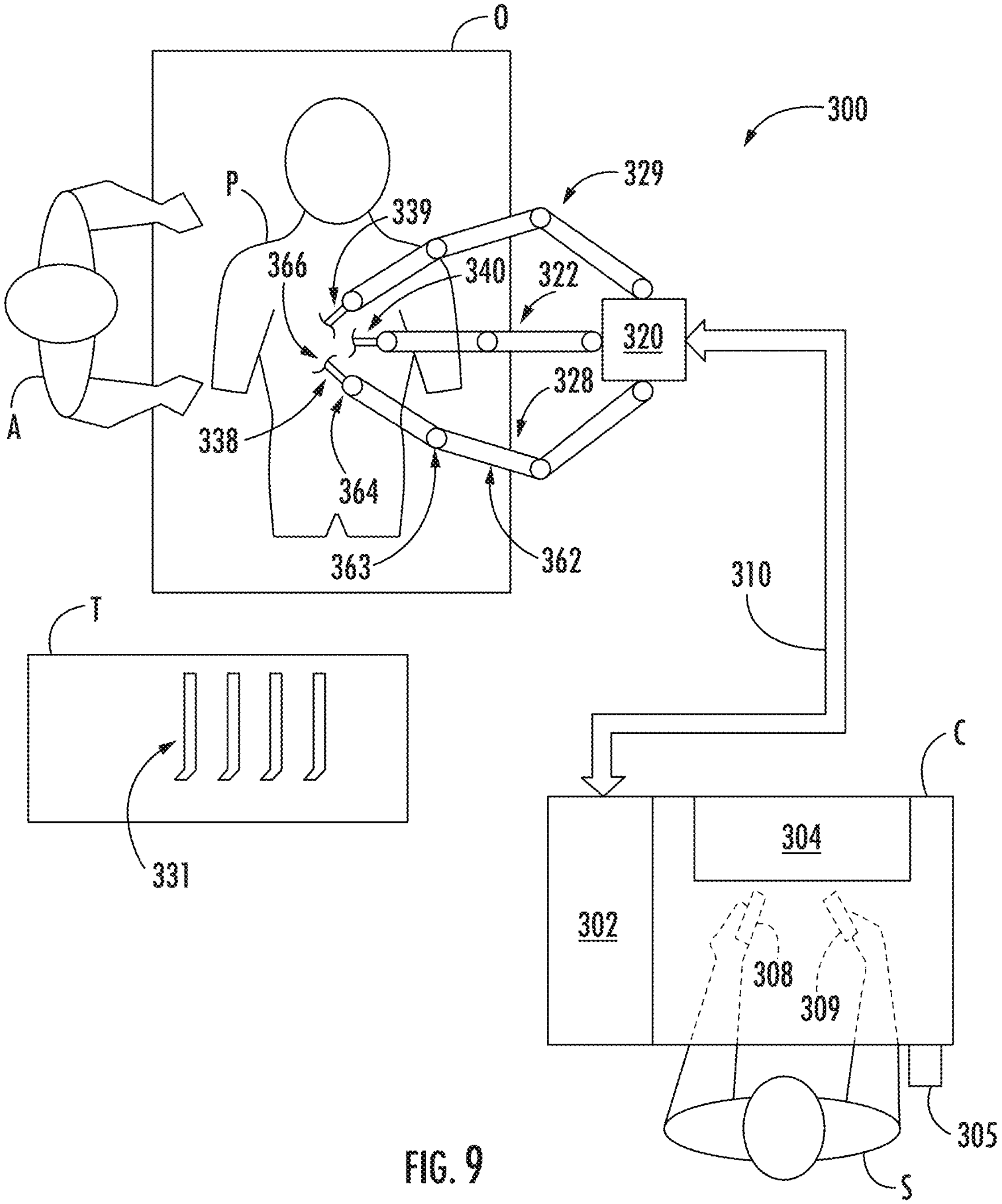
FIG. 9 illustrates a top view of an operating room employing a robotic surgical system utilizing aspects of the present invention.

FIG. 9 illustrates, as an example, a top view of an operating room employing a robotic surgical system. The robotic surgical system in this case is a robotic surgical system 300 including a Console ("C") utilized by a Surgeon ("S") while performing a minimally invasive diagnostic or surgical procedure, usually with assistance from one or more Assistants ("A"), on a Patient ("P") who is lying down on an Operating table ("O").

The Console includes a monitor 304 for displaying an image of a surgical site to the Surgeon, left and right manipulatable control devices 308 and 309, a foot pedal 305, and a processor 302. The control devices 308 and 309 may include any one or more of a variety of input devices such as joysticks, gloves, trigger-guns, hand-operated controllers, or the like. The processor 302 may be a dedicated computer that may be integrated into the Console or positioned next to it.

The Surgeon performs a minimally invasive surgical procedure by manipulating the control devices 308 and 309 (also referred to herein as "master manipulators") so that the processor 302 causes their respectively associated robotic arm assemblies, 328 and 329, (also referred to herein as "slave manipulators") to manipulate their respective removably coupled surgical instruments 338 and 339 (also referred to herein as "tools") accordingly, while the Surgeon views the surgical site in 3-D on the Console monitor 304 as it is captured by a stereoscopic endoscope 340.

Each of the tools 338 and 339, as well as the endoscope 340, may be inserted through a cannula or other tool guide (not shown) into the Patient so as to extend down to the surgical site through a corresponding minimally invasive incision such as incision 366. Each of the robotic arms is conventionally formed of links, such as link 362, which are coupled together and manipulated through motor controlled or active joints, such as joint 363.

The number of surgical tools used at one time and consequently, the number of robotic arms being used in the system 300 will generally depend on the diagnostic or surgical procedure and the space constraints within the operating room, among other factors. If it is necessary to change one or more of the tools being used during a procedure, the Assistant may remove the tool no longer being used from its robotic arm, and replace it with another tool 331 from a Tray ("T") in the operating room.

The monitor 304 may be positioned near the Surgeon's hands so that it will display a projected image that is oriented so that the Surgeon feels that he or she is actually looking directly down onto the operating site. To that end, images of the tools 338 and 339 may appear to be located substantially where the Surgeon's hands are located.

The processor 302 performs various functions in the system 300. One important function that it performs is to translate and transfer the mechanical motion of control devices 308 and 309 to their respective robotic arms 328 and 329 through control signals over bus 310 so that the Surgeon can effectively manipulate their respective tools 338 and 339. Another important function is to implement various control system processes as described herein.

Although described as a processor, it is to be appreciated that the processor 302 may be implemented in practice by any combination of hardware, software and firmware. Also, its functions as described herein may be performed by one unit, or divided up among different components, each of which may be implemented in turn by any combination of hardware, software and firmware. For additional details on robotic surgical systems, see, e.g., commonly owned U.S. Pat. No. 6,493,608 "Aspects of a Control System of a Minimally Invasive Surgical Apparatus," and commonly owned U.S. Pat. No. 6,671,581 "Camera Referenced Control in a Minimally Invasive Surgical Apparatus," which are hereby incorporated herein by reference in their entirety for all purposes.

Figure 10:
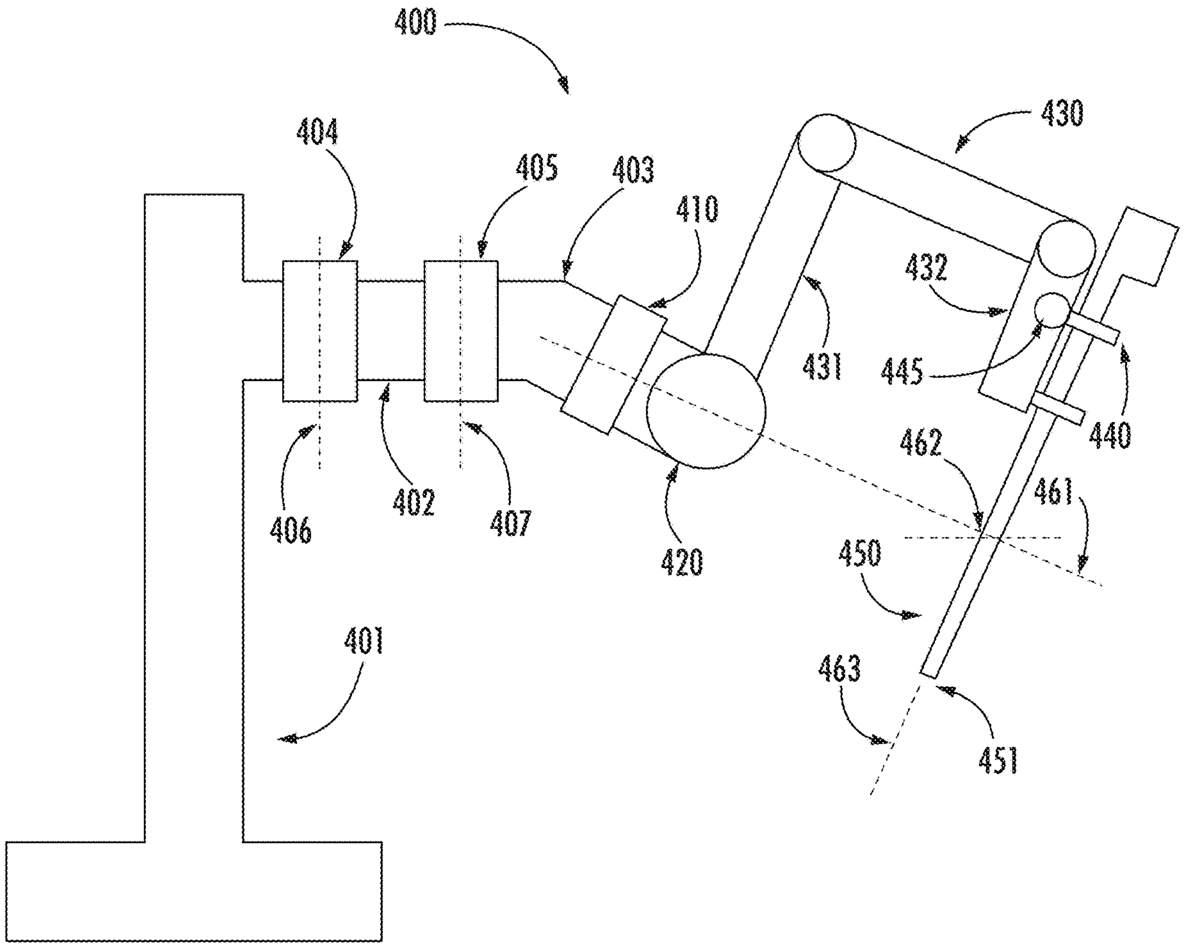
FIG. 10 illustrates a simplified side view of a robotic arm assembly that is usable with various aspects of the present invention.

FIG. 10 illustrates, as an example, a side view of a simplified (not necessarily in proportion or complete) illustrative robotic arm assembly 400 (which is representative of robotic arm assemblies 328 and 329) holding a surgical instrument 450 (which is representative of tools 338 and 339) for performing a surgical procedure. The surgical instrument 450 is removably held in tool holder 440. The arm assembly 400 is mechanically supported by a base 401, which may be part of a patient-side movable cart or affixed to the operating table or ceiling. It includes links 402 and 403, which are coupled together and to the base 401 through setup joints 404 and 405.

The setup joints 404 and 405 in this example are passive joints that allow manual positioning of the arm 400 when their brakes are released. For example, setup joint 404 allows link 402 to be manually rotated about axis 406, and setup joint 405 allows link 403 to be manually rotated about axis 407. Although only two links and two setup joints are shown in this example, more or less of each may be used as appropriate in this and other robotic arm assemblies in conjunction with the present invention. For example, although setup joints 404 and 405 are useful for horizontal positioning of the arm 400, additional setup joints may be included and useful for limited vertical and angular positioning of the arm 400. For major vertical positioning of the arm 400, however, the arm 400 may also be slidably moved along the vertical axis of the base 401 and locked in position.

The robotic arm assembly 400 also includes three active joints driven by motors. A yaw joint 410 allows arm section 430 to rotate around an axis 461, and a pitch joint 420 allows arm section 430 to rotate about an axis perpendicular to that of axis 461 and orthogonal to the plane of the drawing. The arm section 430 is configured so that sections 431 and 432 are always parallel to each other as the pitch joint 420 is rotated by its motor. As a consequence, the instrument 450 may be controllably moved by driving the yaw and pitch motors so as to pivot about the pivot point 462, which is generally located through manual positioning of the setup joints 404 and 405 so as to be at the point of incision into the patient. In addition, an insertion gear 445 may be coupled to a linear drive mechanism (not shown) to extend or retract the instrument 450 along its axis 463.

Although each of the yaw, pitch and insertion joints or gears, 410, 420 and 445, is controlled by an individual joint or gear controller, the three controllers are controlled by a common master/slave control system so that the robotic arm assembly 400 (also referred to herein as a "slave manipulator") may be controlled through user (e.g., surgeon) manipulation of its associated master manipulator. A more complete description of illustrative robotic surgical systems for use with the present invention can be found in commonly-assigned U.S. Pat. Nos. 9,295,524, 9,339,344, 9,358,074, and 9,452,019, the complete disclosures of which are hereby incorporated by reference in their entirety for all purposes.

Hereby, all issued patents, published patent applications, and non-patent publications that are mentioned in this specification are herein incorporated by reference in their entirety for all purposes, to the same extent as if each individual issued patent, published patent application, or non-patent publication were specifically and individually indicated to be incorporated by reference.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of presently disclosed embodiments. Thus the scope of the embodiments should be determined by the appended claims and their legal equivalents, rather than by the examples given.

Persons skilled in the art will understand that the devices and methods specifically described herein and illustrated in the accompanying drawings are non-limiting exemplary embodiments. The features illustrated or described in connection with one exemplary embodiment may be combined with the features of other embodiments. Various alternatives and modifications can be devised by those skilled in the art without departing from the disclosure. Accordingly, the present disclosure is intended to embrace all such alternatives, modifications and variances. As well, one skilled in the art will appreciate further features and advantages of the present disclosure based on the above-described embodiments. Accordingly, the present disclosure is not to be limited by what has been particularly shown and described, except as indicated by the appended claims.

What is claimed is:

1. A surgical instrument comprising:
- a shaft having a longitudinal axis;
- an end effector at a distal end portion of the shaft comprising first and second jaws; and
- a staple cartridge coupled to one of the first or second jaws and comprising one or more staple assemblies, wherein each staple assembly comprises:
  - a staple pusher having a body with upper and lower surfaces and a recess in the upper surface, wherein the recess forms a pocket in the staple pusher, wherein the pocket comprises first and second curved outer surfaces longitudinally spaced from each other and a substantially planar surface extending between the curved outer surfaces; and
  - a staple having first and second legs and a backspan adjoining the first leg to the second leg, wherein the backspan of the staple is configured to reside entirely within the pocket and below the upper surface of the staple pusher.

2. The surgical instrument of claim 1, wherein a transition between each of the first and second legs and the backspan of the staple has a bend radius of 0.015 inches to 0.030 inches.

3. The surgical instrument of claim 1, wherein the first and second curved outer surfaces reside substantially in the recess and below the upper surface of the staple pusher.

4. The surgical instrument of claim 1, wherein the distance from the lower surface of the staple pusher to an inner surface of the recess is less than 60% of a distance between the upper and lower surfaces of the staple pusher.

5. The surgical instrument of claim 1, wherein the staple pusher comprises a support element extending above the recess, wherein the support element comprises a wall at least partially surrounding the recess.

6. The surgical instrument of claim 1, further comprising a drive member configured to move distally through the end effector to move the staple pusher in a substantially perpendicular direction relative to the shaft.

7. The surgical instrument of claim 6, further comprising:

an actuation mechanism in contact with the drive member and configured to translate the drive member distally through the end effector; and an actuator operatively connected to the actuation mechanism, wherein the actuator includes a control device of a robotic surgical system.

8. The surgical instrument of claim 6, wherein the drive member comprises an inclined surface configured to engage the staple pusher upon distal translation of the drive member through the staple cartridge and move the staple from a first position within an interior of the staple cartridge to a second position exterior to the staple cartridge.

9. A staple cartridge for a surgical instrument comprising:

a staple pusher having a body with upper and lower surfaces and a recess in the upper surface, wherein the recess forms a pocket in the staple pusher, wherein the pocket comprises first and second curved outer surfaces longitudinally spaced from each other and a substantially planar surface extending between the curved outer surfaces; and a staple having first and second legs and a backspan adjoining the first leg to the second leg, wherein the backspan of the staple is configured to reside entirely within the pocket and below the upper surface of the staple pusher.

10. The staple cartridge of claim 9, wherein the distance from the lower surface of the staple pusher to an inner surface of the recess is less than 60% of a distance between the upper and lower surfaces of the staple pusher.

11. The staple cartridge of claim 9, wherein the staple has curved portions between each of the first and second legs and the backspan, wherein the curved portions have a bend radius of 0.015 inches to 0.030 inches.

12. The staple cartridge of claim 9, wherein the staple pusher body comprises a support element extending above the recess and wherein the support element comprises a wall extending around at least a portion of the recess and a substantially circumferential wall integral with the staple pusher body.

13. A robotic surgical system comprising:

a surgical instrument comprising an end effector comprising first and second jaws, a drive member configured to translate distally through the end effector and a staple cartridge coupled to one of the first or second jaws, the staple cartridge comprising:

a staple pusher having a body with upper and lower surfaces and a recess in the upper surface, wherein the recess forms a pocket in the staple pusher, wherein the pocket comprises first and second curved outer surfaces longitudinally spaced from each other and a substantially planar surface extending between the curved outer surfaces; and a staple having first and second legs and a backspan adjoining the first leg to the second leg, wherein the backspan of the staple is configured to reside entirely within the pocket and below the upper surface of the staple pusher; and an actuation mechanism in contact with the drive member and configured to translate the drive member distally through the end effector.

14. The robotic surgical system of claim 13, further comprising a robotic arm assembly coupled to the actuation mechanism and a control device coupled to the robotic arm assembly for remotely controlling the actuation mechanism.

15. The robotic surgical system of 14, further comprising a processor configured to transfer motion of the control device to motion of the robotic arm assembly.

16. The robotic surgical system of claim 13, wherein the surgical instrument comprises a shaft having a proximal end and a distal end and a housing on the proximal end of the shaft, wherein the actuation mechanism comprises a motor disposed within the housing and coupled to a robotic arm assembly.

17. The robotic surgical system of claim 13, wherein a transition between each of the first and second legs and the backspan of the staple has a bend radius of 0.015 inches to 0.030 inches.

18. The robotic surgical system of claim 13, wherein the distance from the lower surface of the staple pusher to an inner surface of the recess is less than 60% of a distance between the upper and lower surfaces of the staple pusher.

19. The robotic surgical system of claim 13, wherein the staple pusher comprises a support element extending above the recess, wherein the support element comprises a wall at least partially surrounding the recess.

* * * * *